(12) United States Patent
Davisson et al.

(10) Patent No.: US 8,765,950 B2
(45) Date of Patent: Jul. 1, 2014

(54) REAGENTS FOR BIOMOLECULAR LABELING, DETECTION AND QUANTIFICATION EMPLOYING RAMAN SPECTROSCOPY

(75) Inventors: Vincent Jo Davisson, West Lafayette, IN (US); Shirshendu K. Deb, Bansdroni Kolkata (IN); Giselle Marcelline Knudsen-Mooney, Indianapolis, IN (US); Meiguo Xin, West Lafayette, IN (US)

(73) Assignee: Purdue Research Foundation, Lafayette, IN (US)

( * ) Notice: Subject to any disclaimer, the term of this patent is extended or adjusted under 35 U.S.C. 154(b) by 163 days.

(21) Appl. No.: 13/346,178

(22) Filed: Jan. 9, 2012

(65) Prior Publication Data
US 2012/0107830 A1 May 3, 2012

Related U.S. Application Data

(62) Division of application No. 12/345,071, filed on Dec. 29, 2008, now Pat. No. 8,153,827.

(60) Provisional application No. 61/016,836, filed on Dec. 27, 2007.

(51) Int. Cl.
| C07D 295/00 | (2006.01) |
| G01N 1/00 | (2006.01) |
| G01N 1/18 | (2006.01) |
| G01N 33/00 | (2006.01) |
| G01N 33/92 | (2006.01) |
| G01N 33/48 | (2006.01) |
| G01N 33/566 | (2006.01) |

(52) U.S. Cl.
USPC ............ 544/394; 436/174; 436/177; 436/86; 436/94; 436/71; 436/63; 436/501

(58) Field of Classification Search
None
See application file for complete search history.

(56) References Cited

U.S. PATENT DOCUMENTS

| 6,503,478 B2 | 1/2003 | Chaiken et al. |
| 6,706,892 B1 | 3/2004 | Ezrin et al. |
| 6,750,065 B1 | 6/2004 | White et al. |
| 7,192,778 B2 | 3/2007 | Natan |
| 7,709,169 B2 | 5/2010 | Wu |
| 2003/0211488 A1 | 11/2003 | Mirkin et al. |
| 2005/0089901 A1 | 4/2005 | Porter et al. |

FOREIGN PATENT DOCUMENTS

| EP | 0587008 | 3/1994 |
| WO | WO 2006/037036 | 4/2006 |

OTHER PUBLICATIONS

C. J. Addison and A G. Brolo, Langmuir 22, 8696 (2006).
Ahern, A M.; Garrell, R. L. Langmuir 1988, 4, 1162-1168.
Alban, A; David, S. O.; Bjorkesten, L.; Andersson, C.; Sloge, E.; Lewis, S.; Currie, I., A novel experimental design for comparative two-dimensional gel analysis: Two-dimensional difference gel electrophoresis incorporating a pooled internal standard. Proteomics 2003, 3, (1), 36-44.
Arraez Roman, D.; Efremov, E.; Ariese, F.; Segura Carretero, A; Gooijer, C. Anal. Bioanal. Chem. 2005, 382, 180-5.
R. Bandichhor, A D. Petrescu, A Vespa, A B. Kier, F. Schroeder, and K. Burgess, Bioconjugate Chem. 17, 1219 (2006).
Bantscheff, M., Schirle, M., Sweetman, G., Rick, J., and Kuster, B. (2007) Quantitative mass spectrometry in proteomics: a critical review. Anal. Bioanal. Chem. 389,1017-1031.
E. K. Barefield, G. W. Parshall, and F. N. Tebbe, J. Am. Chem. Soc. 92, 5234 (1970).
S. E. J. Bell, J. N. Mackle, and N. M. S. Sirimuthu, Analyst (Cambridge, U.K.) 130, 545 (2005).
Besada, V., Diaz, M., Becker, M., Ramos, Y., Castellanos-Serra, L., and Fichtner, I. (2006) Proteomics of xenografted human breast cancer indicates novel targets related to tamoxifen resistance. Proteomics 6, 1038-1048.
Campion, A, and Kambhampati, P. (1998) Surface-enhanced Raman scattering. Chem. Soc. Rev. 27, 241-250.
Y. C. Cao, J. Rongchao, and C. A Mirkin, Science 297 (Washington, D.C.), 1536 (2002).
C. J. L. Constantino, T. Lemma, P. A Antunes, P. Goulet, and R. Aroca, Appl. Spectrosc. 57,649 (2003).
P. B. Corio, S. D. M. Brown, A Marucci, M. A Pimenta, K. Kneipp, G. Dresselhaus, and M. S. Dresselhaus, Phys. Rev. B 61, 13202 (2000).
Corthals, G. L., Wasinger, V. C., Hochstrasser, D. F., and Sanchez, J. C. (2000) The dynamic range of protein expression: a challenge for proteomic research. Electrophoresis 21, 1104-1115.
Cunningham, D.; Littleford, R. E.; Smith, W. E.; Lundahl, P. J.; Khan, I.; McComb, D. W.; Graham, D.; Laforest, N. Faraday Discuss. 2006, 132, 135-45.

(Continued)

*Primary Examiner* — James O Wilson
*Assistant Examiner* — Oluwafemi Masha
(74) *Attorney, Agent, or Firm* — Brinks Gilson & Lione

(57) ABSTRACT

The present disclosure provides isotopically substituted compounds of the formula (II):

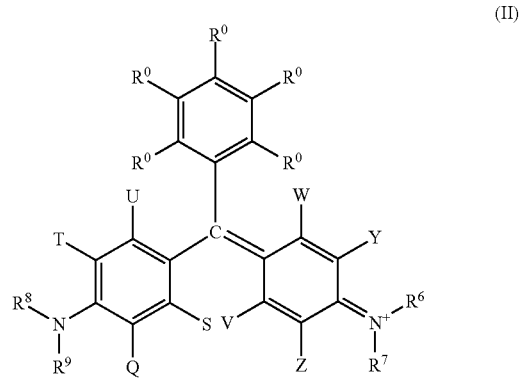

(II)

wherein T, U, V, W, X, Y, Z, $R^0$, $R^3$, $R^4$, $R^5$ and $R^6$ are as defined in the detailed description. The method for detection and quantification using the same is also disclosed.

21 Claims, 16 Drawing Sheets

(56) References Cited

OTHER PUBLICATIONS

Deb, S. K., Davis, B., Ben Amotz, D., Davisson, V., Appl. Spectrosc. vol. 62, No. 9, 2008, 1001-1007.

Deb, S. K., Davis, B., Knudsen, G. M., Gudihal, R., Ben Amotz, D., and Davisson, V. J. Detection and relative quantification of proteins by SERRS using isotopic lables. (2008) J. Am. Chem. Soc. 130, 9624-9625.

V. Derdau, Tetrahedron Lett. 45, 8889, (2004).

Dieringer, J. A, McFarland, A D., Shah, N. C., Stuart, D. A, Whitney, A V., Yonzon, C. R., Young, M. A, Zhang, X. Y., and Van Duyne, R. P. (2006) Surface enhanced Raman spectroscopy: new materials, concepts, characterization tools, and applications. Faraday Discuss. 132, 9-26.

Dieringer, J. A; Lettan, R. B.; Scheidt, K. A; VanDuyne, R. P. J. Am. Chem. Soc. 2007, 129, 16249-16256.

J. D. Driskell, K. M. Kwarta, R. J. Lipert, M. D. Porter, J. D. Neill, and J.F. Ridpath, Anal. Chem. 77, 6147 (2005).

Ebisuya, M., Kondoh, K., and Nishida, E. (2005) The duration magnitude and compartmentalization of ERK MAP kinase activity: Mechanisms for providing signaling specificity. J. Cell Sci. 118, 2997-3002.

Emory, S. R., Haskins, W. E., and Nie, S. (1998) Direct observation of size-dependent optical enhancement in single metal nanoparticles. J. Am. Chem. Soc. 120, 8009-8010.

Evanoff, D. D., Jr., and Chumanov, G. (2005) Synthesis and optical properties of silver nanoparticles and arrays. Chem-PhysChem 6, 1221-1231.

Faulds, K.; Barbagallo, R. P.; Keer, J. T.; Smith, W. E.; Graham, D. Analyst 2004, 129,567-8.

K. Faulds, W. E. Smith, and D. Graham, Analyst (Cambridge, U.K.) 130, 1125 (2005).

K. Faulds, L. Fruk, D. C. Robson, D. G. Thompson, A Enright, E. W. Smith, and D. Graham, Faraday Discuss. 132, 261 (2006).

Filatov Alexander, V., Krotov Grigory, I., Zgoda Victor, G.,and Volkov, Y. (2007) Fluorescent immunoprecipitation analysis of cell surface proteins: a methodology compatible with massspectrometry. J. Immunol. Methods 319, 21-33.

Fujioka, A, Terai, K., Itoh, R. E., Aoki, K., Nakamura, T., Kuroda, S., Nishida, E., and Matsuda, M. (2006) Dynamics of the Ras/ERK MAPK cascade as monitored by fluorescent probes. J. Biol. Chem. 281, 8917-8926.

Gade, D., Thiermann, J., Markowsky, D., and Rabus, R. (2003) Evaluation of two-dimensional difference gel electrophoresis for protein profiling. J. Mol. Microbiol. Biotechnol. 5, 240-251.

J. L. Garnett, T. Mole, R. F. W. Vining, and M. A Long, J. Am. Chem. Soc. 94, 5913 (1972).

Geoghegan, K.F. "Modification of Amino Groups" Current Protocols in Protein Science (1996) (15.2.1-15.2.18).

Gill & von Hippie, Analytical Biochemistry (1989), 182,319-26.

Graham, D., Mallinder, B. J., Whitcombe, D., Watson, N. D., and Smith, W. E. (2002) Simple multiplex genotyping by surface enhanced resonance Raman scattering. Anal. Chem. 74, 1069-1074. 31, 473-84.

Grubisha, D. S.; Lipert, R. J.; Park, H. Y.; Driskell, J.; Porter, M. D. Anal. Chem. 2003, 75, 5936-43.

Han, M. J., Herlyn, M., Fisher, A B., and Speicher, D. W. (2008) Microscale solution IEF combined with 2-D DIGE substantially enhances analysis depth of complex proteomes such as mammalian cell and tissue extracts. Electrophoresis 29, 695-705.

Hanke, S., Besir, H., Oesterhelt, D., and Mann, M. (2008) Absolute SILAC for accurate quantitation of proteins in complex mixtures down to the attomole level. J. Proteome Res. 7, 1118-1130.

N. A. Abu Hatab, J. M. Oran, and M. J. Sepaniak, Am. Chem. Soc. Nano 2,377 (2008).

Heller, C. (2001) Electrophoresis 22, 629-43.

Hirst, M., Haliday, E., Nakamura, J., and Lou, L. (1994) Human GMP synthetase. Protein purification, cloning, and functional expression of cDNA. J. Biol. Chem. 269, 23830-23837.

Ingley, E. (2008) Src family kinases: Regulation of their activities, levels and identification of new pathways. Biochim. Biophys. Acta 1784, 56-65.

Irish, J. M., Czerwinski, D. K., Nolan, G. P., and Levy, R. (2006) Kinetics of B cell receptor signaling in human B cell subsets mapped by phosphospecific flow cytometry. J. Immunol. 177, 1581-1589.

J. B. Jackson and N. J. Halas, Proc. Natl. Acad. Sci. U.S.A. 101, 17930 (2004).

Jensen L., and Schatz, G.C. (2006) J. Phys. Chem. Lett. A 110, 5973-7.

Kalkhof, S., and Sinz, A. (2008) Chances and pitfalls of chemical cross-linking with amine-reactive N-hydroxysuccinimide esters. Anal. Bioanal. Chem. 392, 305-312.

J. H. Kim, J. S. Kim, H. Choi, S. M. Lee, B. H. Jun, K. N. Yu, E. Kuk, Y. K. Kim, D. H. Jeong, M. H. Cho, and Y. S. Lee, Anal. Chem. 78, 6967 (2006).

K. Kneipp, Y. Wang, R. R. Dasari, and M. S. Feld, Appl. Spectrosc. 49, 780 (1995).

Kneipp, K., et al., Phys. Rev. Lett. 1997,78,1667-70.

Kneipp, K., Kneipp, H., Manoharan, R., Hanlon, E. B., Itzkan, I., Dasari, R. R., and Feld, M. S. (1998) Extremely large enhancement factors in surface-enhanced Raman scattering for molecules on colloidal gold clusters. Appl. Spectrosc. 52, 1493-1497.

Kneipp, K., et al., Phys. Rev. E, 1998, 57, R6281-4.

K. Kneipp, H. Kneipp, I. ltzkan, R. R. Dasari, and M. S. Feld, Chem. Rev. 99, 2957 (1999).

Giselle M. Knudsen, Brandon M. Davis, Shirshendu K. Deb, Yvette Loethen, Ravindra Gudihal, Pradeep Perera, Dor Ben-Amotz, and V. Jo Davisson, Bioconjugate Chem., 2008,19 (11), 2212-2220.

Koo, T.-W., et al., Appl. Spectrosc. 2004, 58, 1401-7.

C. Krafft, Anal. Bioanal. Chem. 378, 60 (2004).

Lacy, W. B., Olson, L. G., and Harris, J. M. (1999) Quantitative SERS measurements on dielectric-overcoated silverisland films by solution-deposition control of surface concentrations. Anal. Chem. 71,2564-2570.

LaPlant, F.; Ben-Amotz, D., Design and construction of a microscope-based Raman system. Review of Scientific Instruments 1995,66, (6), 3537-44.

E. E. Lawson, B. W. Barry, A C. Williams, and H. G. M. Edwards, J. Raman Spectrosc. 28, 111 (1997).

D. Lee, S. Lee, G. H. Seong, J. Choo, E. K. Lee, D. G. Gweon, and S. Lee, Appl. Spectrosc. 60, 373 (2006).

Lee, P., and Meisel, D. (1982) Adsorption and surface enhanced Raman of dyes on silver and gold sols. J. Phys. Chem. 86, 3391-3395.

Leimgruber, R. M., Malone, J. P., Radabaugh, M. R., LaPorte, M. L., Violand, B. N., and Monahan, J. B. (2002) Development of improved cell lysis, solubilization and imaging approaches for proteomic analyses. Proteomics 2,135-144.

Lieber, C. A, and Mahadevan-Jansen, A (2003) Automated method for subtraction of fluorescence from biological Raman spectra. Appl. Spectrosc. 57, 1363-1367.

Loethen, Y. L., Zhang, D., Favors, R. N., Basiaga, S. B. G., and Ben-Amotz, D. (2004) Second-derivative variance minimization method for automated spectral subtraction. Appl. Spectrosc. 58, 272-278.

Loethen, Y. L., Knudsen, G. M., Davis, B., Gudihal, R., Davisson, V. J., and Ben- Amotz, D. (2008), J. Proteome Res. 7,1341-1345.

Lopez, M. F., Berggren, K., Chernokalskaya, E., Lazarev, A, Robinson, M., and Patton, W. F. (2000) A comparison of silver stain and SYPRO ruby protein gel stain with respect to protein detection in two-dimensional gels and identification by peptide mass profiling. Electrophoresis 21,3673-3683.

A Lorn, J. Engelbrektsson, C. Eliasson, M. Josefson, J. Abrahamsson, and K. Abrahamsson, Nano Lett. 4,309 (2004).

Lou, L., Nakamura, J., Tsing, S., Nguyen, B., Chow, J., Straub, K., Chan, H., and Barnett, J. (1995) High-level production from a baculovirus expression system and biochemical characterization of human GMP synthetase. Protein Expression Purif. 6, 487-495.

O. Lyandres, N. C. Shah, C. R. Yonzon, J. T. Walsh, Jr., M. R.Glucksberg, and R. P. Van Duyne, Anal. Chem. 77, 6134 (2005).

(56) References Cited

OTHER PUBLICATIONS

MacKeigan, J. P., Murphy, L. O., Dimitri, C. A, and Blenis, J. (2005) Graded mitogen-activated protein kinase activity precedes switch-like c-Fos induction in mammalian cells. Mol. Cell. Biol. 25, 4676-4682.

McHugh, C. J.; Keir, R.; Graham, D.; Smith, W. E. Chem. Commun. 2002, 580-1.

Merril, C. R., Bisher, M. E., Harrington, M., and Steven, A C.(1988) Coloration of silver-stained protein bands in polyacrylamide gels is caused by light scattering from silver grains of characteristic sizes. Proc. Natl. Acad. Sci. U.S.A. 85, 453-457.

Moore, B.D.; Stevenson, L.; Watt, A; Fitsch, S.; Turner, N.J.; Cassidy, C.; Graham, D. Nat. Biotechnol. 2004, 22, 1133-8.

Mortz, E., Krogh, T.N., Vorum, H., and Gorg. A (2001) Improved silver staining protocols for high sensitivity protein identification using matrix-assisted laser desorption/ionixationtime of flight analysis. Proteomics 1, 1359-1363.

S. P. Mulvaney, M. D. Musick, C. D. Keating, and M. J. Natan, Langmuir19, 4784 (2003).

Nam, J. M.; Thaxton, C. S.; Mirkin, C. A Science 2003,301,1884-6.

Nguyen, T.; Francis, M. B. Org. Lett. 2003, 5, 3245-3248.

Nie, S., and Emory, S. R. (1997) Probing single molecules and single nanoparticles by surface-enhanced raman scattering. Science 275, 1102-1106. 80.

Oh, H., Ozkirimli, E., Shah, K., Harrison, M. L., and Geahlen, R. L. (2007) Generation of an analog-sensitive Syk tyrosine kinase for the study of signaling dynamics from the B cell antigen receptor. J. Biol. Chem. 282, 33760-33768.

Oliver, J. C. (2006) Chemical and Structural Dynamics of Guanosine Monophosphate Synthetase. Ph.D. Thesis, Purdue University, W. Lafayette, IN, p. 173 82.

A Pal, N. R. Isola, J. P. Alarie, D. L. Stokes, and T. Vo-Dinh, Faraday Discuss. 132, 293 (2006).

Patton, W. F. (2002) Detection technologies in proteome analysis. J. Chromatography, B: Analyt. Technol. Biomed. Life Sci. 771, 3-31.

Patton,W.F. (2000) Electrophoresis 21,1123-44.

L. D. Qin, S. L. Zou, C. Xue, A Atkinson, G. C. Schatz, and C. A Mirkin, Proc. Natl. Acad. Sci. U.S.A. 103, 13300 (2006).

Ruan, C.; Wang, W.; Gu, B. Anal. Chem. 2006, 78,3379-84.

G. Sabatte, R. Keir, M. Lawlor, M. Black, D. Graham, and W. E. Smith, Anal. Chem. 80, 2351 (2008).

Savitzky, A, and Golay, M. J. E. (1964) Smoothing and differentiation of data by simplified least squares procedures. Anal. Chem. 36, 1627-1639.

Schroeder, S., Zhang, H., Yeung, E. S., Jaensch, L., Zabel, C., and Waetzig, H. (2008) Quantitative gel electrophoresis: sources of variation. J. Proteome Res. 7, 1226-1234.

A M. Schwartzberg, C. D. Grant, A Wolcott, C. E. Talley, T. R. Huser, R. Bogomolni, and J. Z. Zhang, J. Phys. Chem. B 108, 19191 (2004).

Seo, J., Jeong, J., Kim, Y., Hwang, N., Paek, E., and Lee, K.-J. (2008) Strategy for comprehensive identification of posttranslational modifications in cellular proteins, including low abundant modifications: application to glyceraldehyde-3-phosphate dehydrogenase. J. Proteome Res. 7, 587-602.

Shevchenko, A, Wilm, M., Vorm, 0., and Mann, M. (1996) Mass spectrometric sequencing of proteins from silver stained polyacrylamide gels. Anal. Chem. 68, 850-858.

Shi, X., and McGinty, J. F. (2006) Extracellular signal-regulated mitogen-activated protein kinase inhibitors decrease amphetamine induced behavior and neuropeptide gene expression in the striatum. Neuroscience 138, 1289-1298.

Sirover, M. A (2005) New nuclear functions of the glycolytic protein, glyceraldehyde-3-phosphate dehydrogenase, in mammalian cells. J. Cell. Biochem. 95, 45-52.

Smith et al. (2002) Anal. Chem. 74, 3160-7.

Sorensen, B.K. et al. (2002) "Silver Staining of Proteins on Electroblotting Membranes and Intensification of Silver Staining of Proteins Separated by Polyacrylamide Gel Electrophoresis" Anal. Chem. 304, 33-41.

Stover, D. R., Caldwell, J., Marto, J., Root, K., Mestan, J.,Stumm, M., Ornatsky, 0., Orsi, C., Radosevic, N., Liao, L., Fabbro, D., and Moran, M. F. (2004) Differential phosphoprofiles of EGF and EGFR kinase inhibitor-treated human tumor cells and mouse xenografts. Clin. Proteomics 1, 69-80.

Stuart, D. A; Yuen, J. M.; Shah, N.; Lyandres, 0.; Yonzon, C. R.; Glucksberg, M. R.; Walsh, J. T.; Van Duyne, R. P. Anal. Chem. 2006, 78, 7211-7215.

L. Sun, K. B. Sung, C. Dentinger, B. Lutz, L. Nguyen, J. Zhang, H. Qin, M. Yamakawa, M. Cao, Y. Lu, A Chmura, J. Zhu, X. Su, A A Berlin, S. Chan, and B. Knudsen, Nano Lett. 7, 351 (2007).

Tisdale, E. J. (2002) Glyceraldehyde-3-phosphate dehydrogenase is phosphorylated by protein kinase Cill and plays a role in microtubule dynamics in the early secretory pathway. J. Biol. Chem. 277, 3334-3341.

Unlu, M., Morgan, M. E., and Minden, J. S. (1997) Difference gel electrophoresis: a single gel method for detecting changes in protein extracts. Electrophoresis 18, 2071-2077.

Unwin, R. D.; Evans, C. A; Whelton, A D. Trends Biochem. Sci. 2006,31,473-84.

T. Vo-Dinh, F. Van, and M. B. Wabuyele, J. Raman Spectrosc. 36, 640 (2005).

Wabuyele, M. B.; Vo-Dinh, T. Anal. Chem. 2005, 77, 7810-5.

Whitehurst, A, Cobb, M. H., and White, M. A (2004) Stimulus-coupled spatial restriction of extracellular signal regulated kinase 1/2 activity contributes to the specificity of signal-response pathways. Mol. Cell. Biol. 24,10145-10150.

Wolf-Yadlin, A, Hautaniemi, S., Lauffenburger, D. A, and White, F. M. (2007) Multiple reaction monitoring for robust quantitative proteomic analysis of cellular signaling networks. Proc. Natl. Acad. Sci. U.S.A. 104, 5860-5865.

Xie, Y., Jiang, Y., and Ben-Amotz, D. (2005) Detection of amino acid and peptide phosphate protonation using Raman spectroscopy. Anal. Biochem. 343, 223-230.

Zhang, D. M., Xie, Y., Deb, S. K., Davisson, V. J., and Ben-Amotz, D. (2005) Isotope edited internal standard method for quantitative surface-enhanced Raman spectroscopy. Anal. Chem. 77, 3563-3569.

Zhang, R., Sioma, C. S., Wang, S., and Regnier, F. E. (2001) Fractionation of isotopically labeled peptides in quantitative proteomics. Anal. Chem. 73, 5142-5149.

X. Zhang, J. Zhao, A V. Whitney, J. W. Elam, and R. P. Van Duyne, J.Am. Chem. Soc. 128, 10304 (2006).

G. Zheng, L. Qin, and C. A Mirkin, Angew. Chemie Int. Ed. Engl. 47, 1938 (2008).

Juan Cheng, et al., "Enhancement of stimulated Raman scattering of acetone and the generation of three-color laser by using fluorescence dye RB"; Chinese Optics Letters, vol. 3, No. 1, Jan. 10, 2005; pp. 46-48.

Achikanath C. Bhasikuttan, et al., "Efficient Fluorescence Enhancement and Cooperative Binding of an Organic Dye in a Suprabiomolecular Host-Protein Assembly"; Wiley InterScience, Angew. Chem. Int. Ed. 2007, pp. 4120-4122.

Rank: 8  R² = 97.4  RMSECV = 0.264  Bias: 0.00612  RPD: 6.2
Validation No 2 ÷  D0D4 method v1 optimized results without 0 0.q2

Prediction vs True / D4 [pmol] / Cross Validation

Rank: 8  R² = 97.41  RMSECV = 0.264  Bias: -0.00635  RPD: 6.21
Validation No 2 ÷  D0D4 method v1 optimized results without 0 0.q2

REAGENTS FOR BIOMOLECULAR LABELING, DETECTION AND QUANTIFICATION EMPLOYING RAMAN SPECTROSCOPY

CROSS-REFERENCE TO RELATED APPLICATION AND INCORPORATION BY REFERENCE

The present application is a divisional of U.S. Ser. No. 12/345,071 filed Dec. 29, 2008, now U.S. Pat. No. 8,153,827 which in turn claims priority to U.S. Provisional Patent Application No. 61/016,836, filed Dec. 27, 2007, the entirety of which is hereby incorporated by reference.

GOVERNMENT LICENSE RIGHTS

This invention was made with government support under Grant Nos. CA123662 and GM053155 awarded by the National Institute of Health. The government has certain rights in the invention.

FIELD OF THE INVENTION

The present disclosure relates to isotopic reagents, and the methods for detection and quantification using the same.

BACKGROUND OF THE INVENTION

Raman spectroscopy is becoming an increasingly practical technique because of its minimal sample preparation requirements and compatibility with biological materials in aqueous solutions (E. E. Lawson, B. W. Barry, A. C. Williams, and H. G. M. Edwards, J. Raman Spectrosc. 28, 111 (1997); C. Krafft, Anal. Bioanal. Chem. 378, 60 (2004)). Surface-enhanced resonance Raman spectroscopy (SERRS) provides unprecedented enhancement, making it an attractive technique for applications in protein, nucleic acid, and related biomarker analysis (K. Kneipp, H. Kneipp, I. Itzkan, R. R. Dasari, and M. S. Feld, Chem. Rev. 99, 2957 (1999)). SERRS not only overcomes the gap between the inherent sensitivity of Raman scattering and fluorescence, but the Raman spectral features are also larger (and sharper) than fluorescence from the same chromophore (A. Campion and P. Kambhampati, Chem. Soc. Rev. 27, 241 (1998)).

However, SERRS suffers from variability in enhancement of Raman intensity depending upon the nanomorphology of the substrate (typically silver colloids), thereby affecting the reproducibility of the measurement. Several approaches to addressing problems associated with the reproducibility and optimization of SERRS have been reported. One strategy involves the linkage of SERRS active molecules and analyte-binding molecules with the surface of SERRS enhancing particles (U.S. Patent Publication No. 2005/0089901). The correction of the variation of SERRS signals is also accomplished using either an internal or an external standard. The use of an isotopic-edited internal standards (IEIS) method was reported to improve the performance of SERRS with unprecedented accuracy (Zhang, D. M., et al. Anal. Chem. 2005, 77, 3563-69). The internal standardization prototype study used two isotopic variants of the rhodamine 6G (R6G) chromophore.

SERRS active molecules have been employed as labeling reagents for bioanalytical applications. Several classes of organic dyes have been reported as SERS active molecules since they exhibit high Raman cross-sections and offer single molecule detection. The most widely used dyes are rhodamine (xanthene class), crystal violet (triarylmethane class), and nile blue (oxazine class). Single molecule detection limits have been reported for rhodamine 6G, crystal violet, nile blue, and other SERRS active molecules (Kneipp, K., et al., Phys. Rev. E, 1998, 57, R6281-4; Koo, T.-W., et al., Appl. Spectrosc. 2004, 58, 1401-7; Nie, S., et al., Science, 1997, 275, 1102-6; Kneipp, K., et al., Phys. Rev. Lett. 1997, 78, 1667-70).

A number of studies have been undertaken on SERRS or SERS for biomolecular detection. For example, Mirkin et al. (U.S. Patent Publication No. 2003/0211488) employed a dye-conjugated gold particle for identification of target DNA sequences. Rhodamine 6G-NHS ester derivative was used to label oligonucleotides. Also a bar coding strategy using multiple dyes created unique labels. However, isotopic variants of R6G were not disclosed in this patent, nor was the composition of dye envisioned for determination of analyte quantities.

Chaiken, J. et al. (U.S. Pat. No. 6,503,478) disclosed deuterated labeling agents and their Raman spectroscopy for tissue imaging. However, this patent only names small deuterated molecules for labeling, and is meant more for imaging and contrasting agents. Quantification by the reagents is not described.

An immunoassay displacement method for detecting the presence of or amount of a target analyte was described by White, P. C., et al. (U.S. Pat. No. 6,750,065). An antibody is bound to an analyte analog, which is labeled with a Raman active tag. The labeled analog is replaced by the analyte in an unknown sample. The released labeled analog interacts with a SERS or SERRS substrate and generates Raman signal. This method was envisioned as a drug detection and quantification method. However, the method is limited to a very specific format of immunoassay.

Another patent (EP Patent No. 0587008 to Tarcha, P. J.) described a composition, a kit, and a device for the determination of the presence or amount of an analyte. The composition comprises a specific binding member, a Raman-active label, and a substrate having a surface capable of inducing a surface-enhanced Raman light scattering. The test mixture was illuminated with a radiation sufficient to cause the Raman-active label in the test mixture to emit a detectable Raman spectrum. The differences in the detected surface-enhanced Raman scattering spectra depend upon the amount of the analyte present in the test mixture. Thus, by monitoring these differences, the presence or amount of the analyte are determined. This patent does not discuss multiplexing analysis.

Another approach was disclosed in U.S. Pat. No. 7,192,778 (Natan, M. J). Metal nanoparticles were associated with Raman-active dyes and surrounded by an encapsulant. The metal nanoparticles were used as sensitive optical tags detectable by SERRS.

Isotopic variants of Rhodamine 6G have been used for relative quantification (PCT Publication No. WO 2006/037036). It is desirable to extend the approach to more isotopic variants of Rhodamine dyes and other classes of dyes.

BRIEF SUMMARY OF THE INVENTION

The present disclosure is directed to isotopically substituted reagents and the methods for detection and quantification using the same.

In one embodiment, the disclosed compounds are of the formula (I):

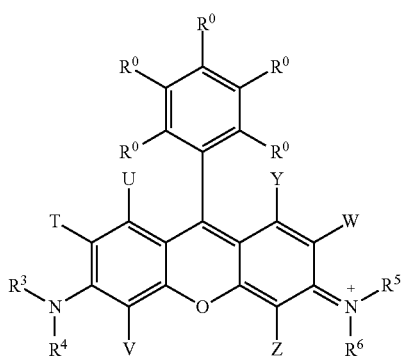

where T, U, V, W, X, Y, Z, $R^0$, $R^3$, $R^4$, $R^5$, and $R^6$ are as defined below.

In another embodiment, the disclosed compounds are of the formula (II):

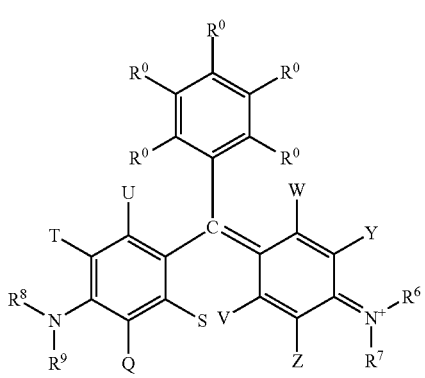

where Q, S, T, U, V, W, X, Y, Z, $R^0$, $R^6$, $R^7$, $R^8$, and $R^9$ areas defined below.

In yet another aspect, a method for evaluating an analyte is disclosed. The method comprises labeling at least a portion of an analyte with any compound disclosed in the present disclosure, and detecting the labeled portion.

In still another aspect, a method for multiplex analysis is disclosed. The method comprises labeling the analytes with the compounds disclosed in the present disclosure, and detecting the analytes.

BRIEF DESCRIPTION OF THE FIGURES

In FIG. 3B is shown the spectral region containing the 600 and 611 cm$^{-1}$ peaks indicative of d0 and d4-R6G labels respectively

DETAILED DESCRIPTION OF THE DISCLOSURE

Figure 1:
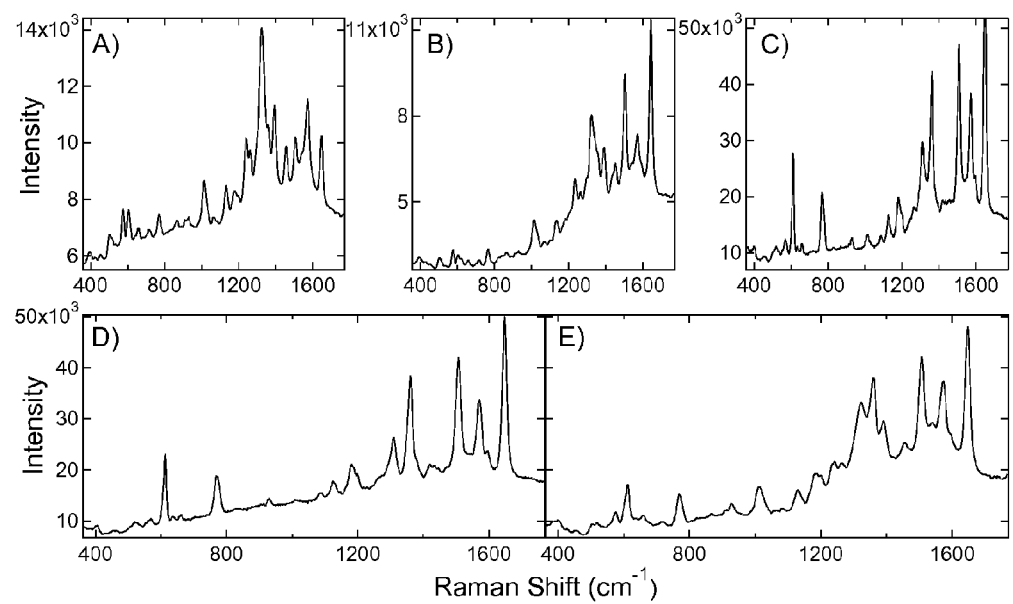
FIG. 1 is a graph of the SERRS spectra of 10 nM samples of three different rhodamine dyes. (A) Rhodamine 19 perchlorate. (B) Rhodamine 101. (C) R6G. (D) Mixture of rhodamine 19:rhodamine-101:R6G at a ratio of 3:3:1. (E) Simulated spectrum of the mixture of R-19, R-101, and R6G at a ratio of 3:3:1.

The present disclosure is directed to the isotopically substituted reagents, and their use for detection and quantification employing Raman spectroscopy.

Definitions

When describing the compounds, compositions, methods and processes of this disclosure, the following terms have the following meanings, unless otherwise indicated.

The term "rhodamine" refers to any compound that comprises a parent rhodamine ring or an extended rhodamine ring, including any substituted versions of the same, wherein substitutions can be made at any one or all of the 1-, 2-, 2'-, 4-, 4'-, 5'-, 5-, 7', 7-, 8- and 9-carbons and/or at any one or both of the exocyclic amino and imino nitrogens.

The term "crystal violet" refers to any compound that comprises a parent Crystal Violet structure or an extended crystal violet phenyl ring, including any substituted versions of the same, wherein substitutions can be made at any one or all of the 2-, 3-, 4-, 5-, 2'-, 3'-, 4'-, 5'-, 2"-, 3"-, 4"-5"-, and central-carbon and/or at any one or both of the exocyclic amino and imino nitrogens.

The term "malachite green" refers to any compound that comprises a parent Malachite Green structure or an extended malachite green phenyl ring, including any substituted versions of the same, wherein substitutions can be made at any one or all of the 2-, 3-, 4-, 5-, 2'-, 3'-, 4'-, 5'-, 2"-, 3"-, 4"-5"-, and central-carbon and/or at any one or both of the exocyclic amino and imino nitrogens.

The term "poly" when used as a prefix in the name of a polymer, refers to a polymer made up in the majority of the monomer or monomers that follow the prefix.

The term "particles" refers to solid masses that are spherical or irregular in shape.

The term "biomolecule" refers to a molecule of a type typically found in a biological system, whether such molecule is naturally occurring or the result of some external disturbance of the system (e.g., a disease, poisoning, genetic manipulation, etc.), as well as synthetic analogs and derivatives thereof. Non-limiting examples of biomolecules include amino acids (naturally occurring or synthetic), peptides, polypeptides, glycosylated and unglycosylated proteins (e.g., polyclonal and monoclonal antibodies, receptors, interferons, enzymes, etc.), nucleosides, nucleotides, oligonucleotides (e.g., DNA, RNA, PNA oligos), polynucleotides (e.g., DNA, cDNA, RNA, etc.), carbohydrates, hormones, haptens, steroids, toxins, etc. Biomolecules may be isolated from natural sources, or they may be synthetic.

The term "ferritin" refers to a globular protein complex consisting of 24 protein subunits and is the main intracellular iron storage protein in both prokaryotes and eukaryotes, keeping it in a soluble and non-toxic form.

The term "PNA" refers to peptide nucleic acid. It is an artificially synthesized polymer similar to DNA or RNA.

The term "recombinant DNA" means a form of synthetic DNA that is engineered through the combination or insertion of one or more DNA strands.

The term "lysate" refers to the solution produced when cells are destroyed by disrupting their cell membranes.

The term "metabolites" refers to the intermediates and products of metabolism.

The term "isotopomers" (isotopic isomers) refers to isomers having the same number of each isotopic atom but differing in their positions.

The term "hGMPS" refers to human guanine monphosphate synthetase. It is an enzyme that converts xanthosine monophosphate to guanosine monophosphate.

The term "HCT116" refers to human colorectal carcinoma cell line.

The term "analyte" is a molecule or substance to be measured or assayed.

The term "hydroxy" means the —OH group.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "alkenyl" means a hydrocarbon group that contains at least one carbon-to-carbon double bond. The term "alkynyl" means a hydrocarbon group that contains at least one carbon-to-carbon triple bond. Alkenyl and alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "substituent" means an atom or a group that replaces another atom or group in a molecule.

All of the above terms (e.g., "alkyl," "aryl," "heteroaryl" etc.), in some embodiments, include both substituted and unsubstituted forms of the indicated groups. These groups may be substituted multiple times, as chemically allowed.

Compounds

The labeling reagents used for this disclosure can be, for example, organic dyes with different isotopic substituents, such as the substitution of some hydrogen atoms for deuterium atoms. The substitution can be employed in such SERRS active dyes such as xanthene dyes like rhodamine and fluorescein, triarylmethane dyes like crystal violet, azo dyes like benzotriazole azo, mercaptopyridine, and others. The isotopic variants of the reagents can be obtained through the use of isotopically substituted precursors of the dye-forming reaction. The isotopic variants may also be obtained by isotopic exchange of the labile aromatic protons of the chromophore by heating the dye in a deuterated acidic media.

In one embodiment, the compound of the present disclosure is of the formula (I):

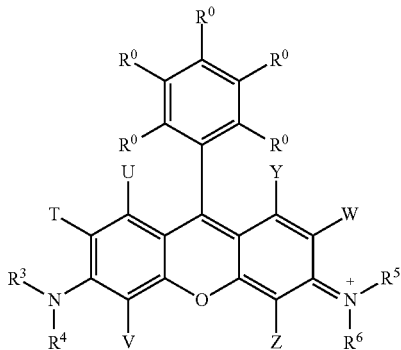

where $R^0$ is either X or —C(O)NR$^1$R$^2$, provided that at least one of $R^0$ is —C(O)NR$^1$, R$^2$, where T, U, V, W, X, Y, and Z are each independently hydrogen, deuterium, halogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, or substituted or unsubstituted 3- to 10-membered heterocyclyl, where at least one of T, U, V, W, X, Y, and Z is deuterium, where $R^1$ is hydrogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, or substituted or unsubstituted 3- to 10-membered heterocyclyl, where $R^2$ is substituted or unsubstituted $C_{2-8}$ alkynyl, —R'N$_3$, —R'COOH, —R'C(O)OR", R'C(O)NH$_2$, —R'NCS, —R'NCO, —R'NH$_2$, —R'SH, —R'NC(O)CH$_2$I, or —R'C(O)O-succinimide, where $R^3$, $R^4$, $R^5$, and $R^6$ are each independently hydrogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, or substituted or unsubstituted 3- to 10-membered heterocyclyl, where $R^1$ and $R^2$, $R^3$ and $R^4$, or $R^5$ and $R^6$ may, together with the atoms to which they are attached, form a substituted or unsubstituted 3- to 10-membered ring, and where R' and R" are each independently selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl.

In one embodiment, $R^2$ in the formula (I) is —(CH$_2$)$_n$N$_3$, —(CH$_2$)$_n$NH$_2$, —(CH$_2$)$_n$COOH, —(CH$_2$)$_n$C(O)OR", —(CH$_2$)$_n$C(O)NH$_2$, —(CH$_2$)$_n$NCS, —(CH$_2$)$_n$NCO, —(CH$_2$)$_n$NH$_2$, —(CH$_2$)$_n$SH, —(CH$_2$)$_n$NC(O)CH$_2$I, —(CH$_2$)$_n$C(O)O-succinimide, —(CH$_2$)$_n$C≡CH, —(CH$_2$)$_n$Ar$^1$NCS, —(CH$_2$)$_n$Ar$^1$NH$_2$, —(CH$_2$)$_n$NC(O)CH$_2$C≡CH, or —(CH$_2$)$_n$C(O)NCH$_2$CH$_2$SH. n is 1-10, and Ar$^1$ is substituted or unsubstituted $C_{6-10}$ aryl, substituted or unsubstituted 5- to 10-membered heteroaryl, or substituted or unsubstituted 3- to 10-membered heterocyclyl.

In another embodiment, in formula (I), T and W are hydrogen. In another embodiment, in formula (I), T and W are methyl.

In another embodiment, in formula (I), $R^3$ and $R^5$ are hydrogen. In another embodiment, in formula (I), where $R^4$ and $R^6$ are ethyl.

In another embodiment, in formula (Ia), at least one of $R^0$ is —C(O)-substituted or unsubstituted piperazine. In another embodiment, the at least one of $R^0$ is of the formula (Ia) or (Ib):

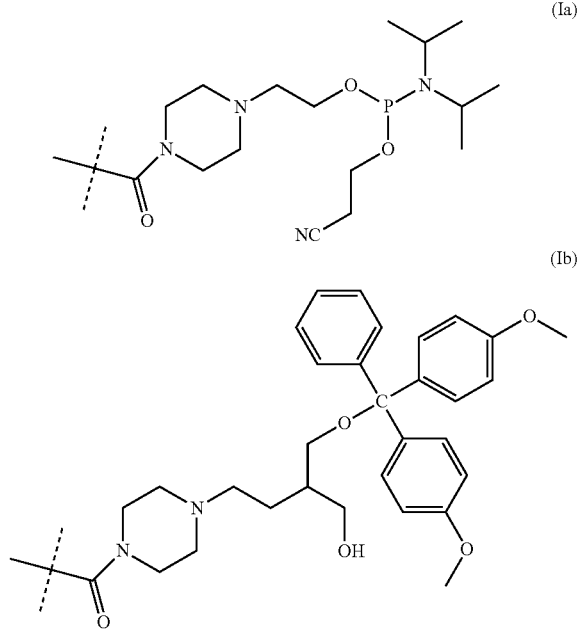

In another embodiment, the compound of the present disclosure is of formula (II):

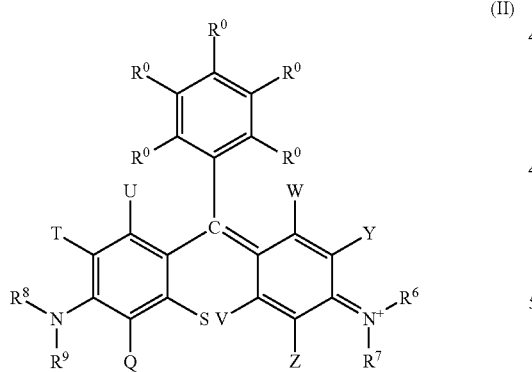

where $R^0$ is either X or of the formula (IIa),

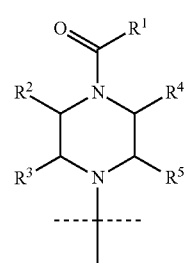

provided that at least one of $R^0$ is of the formula (IIa), where Q, S, T, U, V, W, X, Y, and Z are each independently hydrogen, deuterium, halogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, or substituted or unsubstituted 3- to 10-membered heterocyclyl, where at least one of Q, S, T, U, V, W, X, Y, and Z is deuterium, where $R^1$ is substituted or unsubstituted $C_{2-8}$ alkynyl, —R'$N_3$, —R'COOH, —R'C(O)OR'', —R'C(O)$NH_2$, —R'NCS, —R'NCO, —R'$NH_2$, —R'SH, —R'NC(O)$CH_2$I, or —R'C(O)O-succinimide, where $R^2$, $R^3$, $R^4$, $R^5$, $R^6$, $R^7$, $R^8$, and $R^9$ are each independently hydrogen, halogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{8-10}$ aryl, substituted or unsubstituted 5- to 10-membered heteroaryl, or substituted or unsubstituted 3- to 10-membered heterocyclyl, where $R^2$ and $R^3$, $R^4$ and $R^5$, $R^6$ and $R^7$, or $R^8$ and $R^9$ may, together with the atoms to which they are attached, form a substituted or unsubstituted 3- to 10-membered ring, and where R' and R'' are each independently selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{8-10}$ aryl, substituted or unsubstituted 5- to 10-membered heteroaryl, and substituted or unsubstituted 3- to 10-membered heterocyclyl.

In one embodiment, in formula (II), $R^1$ is —$(CH_2)_nN_3$, —$(CH_2)_nNH_2$, —$(CH_2)_nCOOH$, —$(CH_2)_nC(O)OR''$, —$(CH_2)_nC(O)NH_2$, —$(CH_2)_nNCS$, —$(CH_2)_nNCO$, —$(CH_2)_nNH_2$, —$(CH_2)_nSH$, —$(CH_2)_nNC(O)CH_2I$, —$(CH_2)_nC(O)O$-succinimide, —$(CH_2)_nC\equiv CH$, —$(CH_2)_nAr^1NCS$, —$(CH_2)_nAr^1NH_2$, —$(CH_2)_nNC(O)CH_2C\equiv CH$, or —$(CH_2)_nC(O)NCH_2CH_2SH$. n is 1-10. $Ar^1$ is substituted or unsubstituted $C_{8-10}$ aryl, substituted or unsubstituted 5- to 10-membered heteroaryl, or substituted or unsubstituted 3- to 10-membered heterocyclyl.

In another embodiment, where the at least one of $R^0$ is of the formula of formula (IIb or IIc):

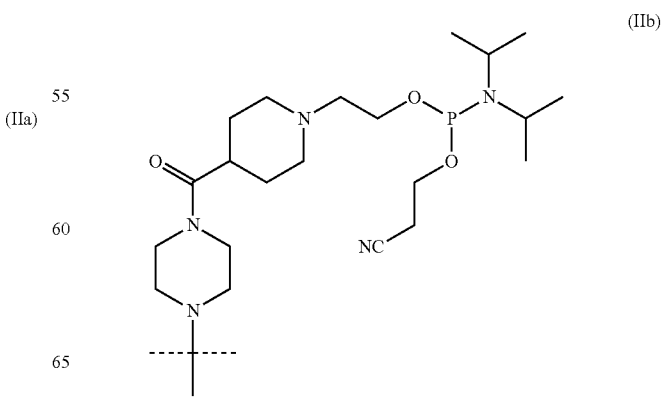

(IIc)

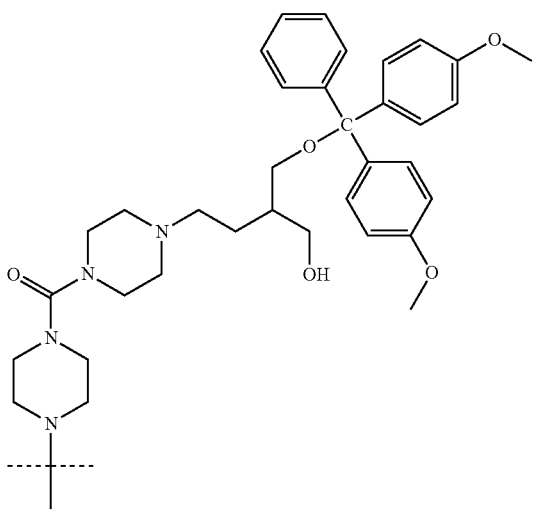

Detection and Quantification

The present disclosure provides a method for evaluating a sample comprising the steps of: (a) labeling at least a portion of an analyte with any compound disclosed in the present disclosure, and (b) detecting the labeled portion. The method can optionally further comprise any of the following steps: (c) labeling at least a portion of the analyte with a non-isotopic compound, (d) separating the analyte from the sample, (e) applying particles onto the analyte, and (f) applying the analyte onto a substrate. The non-isotopic compound has the same chemical structure as the compound in step (a), and only differs in non-isotopic substitution.

The present disclosure also provides a method for multiplex analysis comprising the steps of: (a) labeling a plurality of analytes with at least two compounds disclosed in the present disclosure, and (b) detecting the labeled analytes. The method can optionally further comprise any of the following steps: (c) labeling at least the analytes with a non-isotopic compound, (d) separating the analytes from the sample, (e) applying particles onto the analytes, and (f) applying the analytes onto a substrate. The non-isotopic compound has the same chemical structure as the compound in step (a), and only differs in non-isotopic substitution.

The analyte can be labeled covalently. The isotopic reagents can be functionalized for incorporation of the analyte. The functional groups can be any group known in the art, such as alkynyl, azide, carboxylic acid, ester, amide, thiocyanate, cyanate, amine, thiol, cyanide, succinimide, maleimide, and the like. The preferred example is N-hydroxy-succimide (NHS)-ester. For example, the labeling can be achieved by using a common method developed for N-hydroxy-succimide (NHS)-ester linked dyes (Patton, W. F., Journal of Chromatography B, 2002, 771, (1-2), 3-31). This labeling method provided labeling efficiency of 1-2% and was verified by monitoring the UV-visisble absorbance spectrum and determining the molar amounts of dye and protein in the sample. Alternatively, the labeling can be achieved by other methods.

The separating includes sodium dodecyl sulfate-polyacrylamide gel electrophoresis (SDS-PAGE), two-dimensional SDS-PAGE (2-DGE), western blot, and other separation techniques known in the art.

The substrate can be polymeric membranes (such as nitrocellulose, polyvinylidene fluoride (PVDF), or polysulfone), polymeric gels, or polymeric beads. Alternate substrates can be any materials with a semi-permeable or a permeable surface, such as paper or chromatographic material, in so far as they are able to cause aggregation of biomolecules with labeling reagent and silver particles. These surfaces can serve as immobilization surfaces for proteins, nucleic acids or other biomolecule samples.

The particles can be any combination of known SERRS active metals of different shapes (spherical or nano-rod). Preferably, the particles comprise metallic materials. The examples include copper, silver, and gold nanoparticles. Silver particle deposition can be accomplished using either standard protein gel silver staining (Mortz, E., et al., Proteomics 2001, 1, (11), 1359-63; Shevchenko, A., et al., Anal. Chem. 1996, 68, 850-858) or commercial silver enhanced gold stains (Ted Pella). For optimized SERRS signal enhancement, the silver particles can be prepared by modifying the sizes and shapes (Emory, S. R., et al., 1998, J. Amer. Chem. Soc. 120, (31), 8009-10; Evanoff, D. D., Jr., et al., 2000, Chem. Phys. Chem. 6, (7), 1221-31).

The isotopic edited internal standard (IEIS) approach is used for quantitative detection. SERRS from dye molecules even within the same structural class display distinct spectral intensities that are not proportional to analyte concentrations. For example, the actual spectrum of the mixture of rhodamine 19 perchlorate, rhodamine 101, and rhodamine 6G (R6G) bears limited resemblance to that expected for an ideally additive system (FIG. 1). The result suggested that the dyes of different structures are not suitable in internal standardization and quantification of SERRS. In contrast, the use of isotopomers of the same Raman probe as the internal standard in SERRS can overcome the difficulties in matching the dye-substrate affinities of different dyes, because those for isotopic variants of a single dye are nearly identical. The preferred embodiments include the isotopic variants of R6G-d0/d2, R6G-d0/d4, rhodamine B-d0/d2, nile blue-d0/d2, crystal violet-d0/d6, and malachite green-d0/d4. Using isotope edited dye pairs ensures that the resultant SERRS patterns accurately reflect true mixture compositions since the intensities for the isotopomeric probes remain constant irrespective of the absolute enhancement factors. The structures of the isotopic dye pairs are almost identical and they equally compete for "hotspots" within the concentration ranges. The relative quantification using IEIS enables accurate, reproducible (residual standard deviation ±2.2%) concentration measurements over a range of 200 pM to 2 μM.

Figure 3:
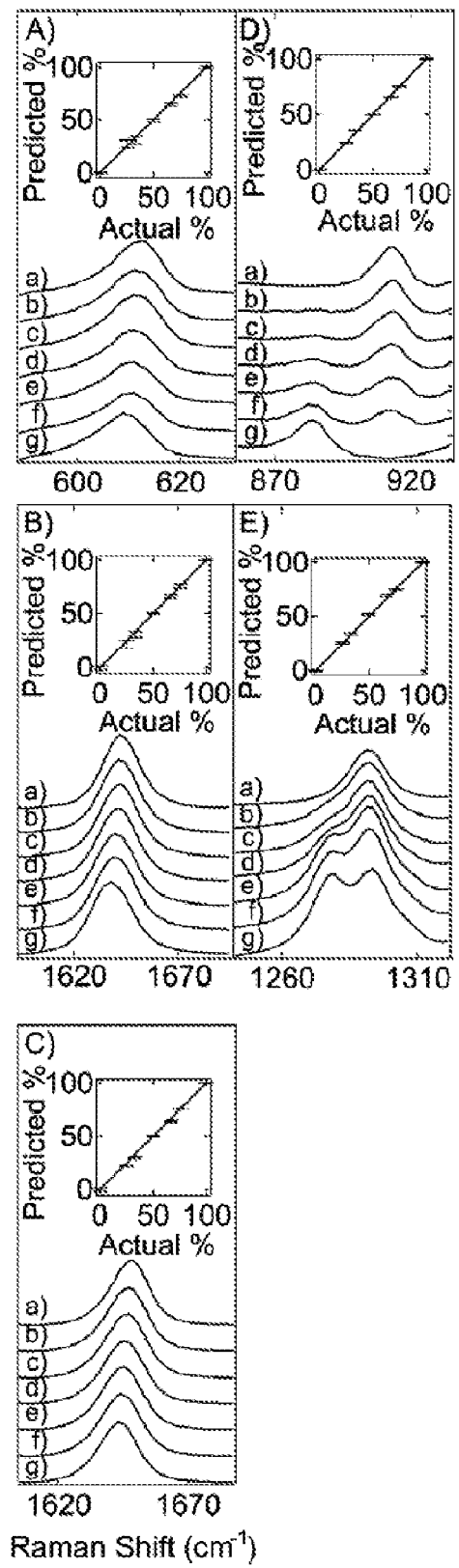
FIG. 3 is a graph of SERRS spectra of mixtures of each dye (d0/dX) pair. The relative d0/dX dye concentrations are (a) 100/0, (b) 75/25, (c) 67/33, (d) 50/50, (e) 33/67, (f) 25/75, and (g) 0/100. (A) SERRS spectra of R6G-d0/d2. (B) Rhodamine B-d0/d2. (C) Nile blue-d0/d2. (D) Crystal violet-d0/d6. (E) Malachite green-d0/d4. The insets are the predicted percentage of dX versus the actual percentage dx of each ratio. The error bars represent one standard deviation. Spectra are scaled and offset for improved visualization.

Several distinctions of the spectra for R6G-d0/d2 and the previously reported R6G-d4 provide the potential of multiplex analysis. As an example, shown in FIG. 3 is the R6G-d0 signal at 613 $cm^{-1}$, which shifts to 609 $cm^{-1}$ for R6G-d2 and to 602 $cm^{-1}$ for RG6-d4. Therefore, multiple samples can be analyzed by using the labeling reagents, which have the same chemical structures and differ only in isotopic substitution and functional groups.

Figure 4:
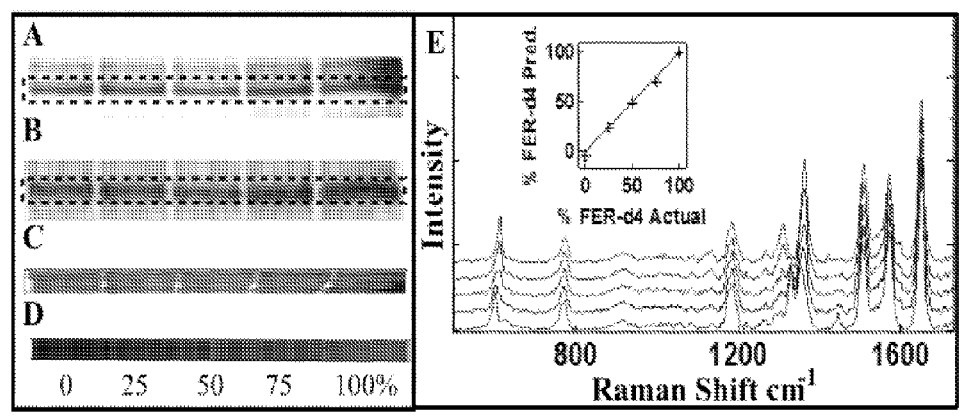
FIG. 4 illustrates an SDS-PAGE gel analysis of 0, 25, 50, 75 and 100% d4-R6G mixtures of d0- and d4-R6G-labeled ferritin. Each lane was loaded with a total of 20 pmol of dye or 0.7 μg protein. (A) The 20 kDa protein band stained with silver was imaged with white light. (B) The 20 kDa protein band was imaged by fluorescence using 532 nm excitation and a 580 nm emission filter. (C) SERRS intensity was normalized to the most intense signal in the image of the boxed region in A and B. (D) A color coded image representation of the percent of R6G-d4 label (blue corresponds to 100% R6G-d4 label, and red corresponds to 100% R6G-d0-label). (E) The fluorescence baseline-subtracted SERRS-spectra of the five mixtures. The spectral shifts at 600 cm$^{-1}$ were used to calculate the percent isotopic compositions for d0- and d4-R6G corresponding to the relative amounts of the two ferritin samples. The inset of E shows the percent d4-R6G composition determined by general least squares fitting of spectra from the ratio lanes. The error bars represent the 95% confidence interval for five measurements taken from each ratio lane.

In one embodiment, ferritin samples labeled with d0- or d4-R6G were mixed in varied ratios and separated on SDS PAGE (FIG. 4). To obtain SERRS in a gel matrix, in situ formation of silver nanoparticles using a protein silver staining protocol was pursued (Ahern, A. M.; Garrell, R. L. Langmuir 1988, 4, 1162-1168; Shevchenko, A.; Wilm, M.; Vorm, O.; Mann, M. Anal. Chem. 1996, 68, 850-858). Protein Raman signals were not observed in the surface enhanced R6G spectra presumably due to larger SERRS enhancements for the dye-surface interactions. Formation of an SERRS active silver nanoparticle enhancement agent within a polymeric matrix offers a practical approach to biomolecular detection after capture or separation from biological mixtures. The spectra in the immobilized labeled protein accurately reflect the relative molecular content.

In another embodiment, multiple protein isoforms within a complex biological sample background were detected and quantified by IEIS method. R6G-protein encoding has enabled the absolute quantification of sample in hydrated gels using water-internal standardized fluorescence spectral imaging. The particular combination of chemical features in d0- and d4-R6G labeling reagents and in situ silver nanoparticle formation around protein in a gel matrix has enabled highly accurate relative quantification using SERRS detection with an established protein separation workflow. Three major species of human GMP synthetase were quantified. In a single-point determination mode, purified recombinant hGMPS species could be quantified in single gels with a 1-6% error over a 1 μg to 1 ng protein mass range. In an imaging application using automated spectral analysis, an RSD % of 16% could be obtained.

The method of the disclosure can be used to quantify proteins, nucleic acids, lipids, their structural mimetics, fragments, metabolites, or any analyte from biological fluids, cells, or tissues. The fields of use for these reagents, methods include bioscience research, pharmaceutical discovery and development, biopharmaceutical manufacturing, food safety, clinical diagnostics, biohazard detection, or forensic assessment.

EXAMPLES

Synthesis of Reagents

Methods and Materials. All solvents and reagents were purchased from Aldrich. Reactions were monitored by thin layer chromatography (TLC) using precoated silica gel plates (60 F254). Column chromatography was performed using 230-400 mesh silica gel. The dyes obtained commercially were further purified by flash column chromatography using, dichloromethane/methanol mixture both before and after isotopic exchange. $^1$H NMR spectra were acquired on a 300, 400 or 500 MHz spectrometer. The chemical shifts of the protons are given in parts per million (δppm) with respect to tetramethylsilane as internal standard. High resolution mass spectra were obtained using electrospray ionization.

Efficient synthesis of the linker N-methylhexanlmethyl ester was achieved by acid hydrolysis of N-methyl caprolatam in the presence of concentrated HCl and methanol with a yield of 95%.

Isotopomeric dyes were synthesized by isotopic exchange procedure or using deuterated precursors. Scheme 1 represents the synthesis of R6G-d0 and -d4 labeling active reagents for protein labeling. The precursors of d0-R6G-acid and d4-R6G-acid were coupled to the linker of N-methylhexanlmethyl ester. The resulted methyl esters were hydrolyzed under basic condition to afford the corresponding acids, which were transformed to their NHS esters in the presence of a coupling reagent and N-hydroxysuccinimide ester.

Scheme 1.

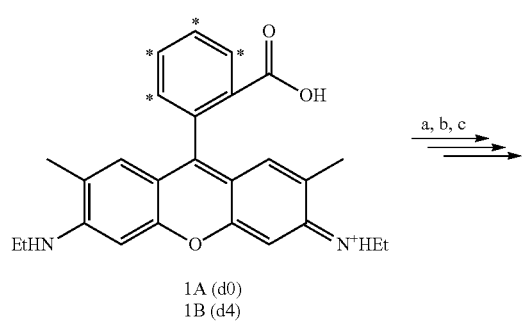

1A (d0)
1B (d4)

-continued

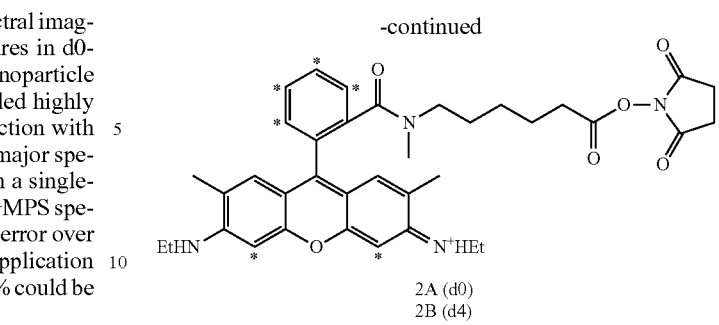

2A (d0)
2B (d4)

Reagents and conditions:
a HATU/DIPEA/NHMe(CH2)5CO2Me/DMF, 65%;
b Ba(OH)2/MeOH—H2O, 45%;
c (iii) HATU/DIPEA/NHS/DMF, 80%. (NHS) N-hyrdoxysuccinimide ester).
The sites of deuterium are noted with an asterisk.

Example of Synthesis.

One part of 3-ethylaminop-cresol was added to one part of d4-phthalic anhydride in o-dicholorobenzene at 170° C. with vigorous stirring. Another part of 3-ethylamino-p-cresol was added in five portions, with each addition separated by 1 h. The reaction was continued for 4 hours following the final after addition. After cooling the reaction mixture to room temperature, 3% aqueous sodium hydroxide solution was added followed by acidifying the mixture with concentrated hydrochloric acid. The mixture was filtered, washed with diethyl ether to obtain a red solid which was dried under vacuum to yield the crude product of rhodamine 6G acid (d4). To a stirring solution of the above compound (100 mg, 0.22 mmol) in anhydrous DMF (2 mL) was added O-(benzotriazol-1-yl)-N,N,N',N'-tetramethyluronium hexafluorophosphate (91 mg, 0.242 mmol) followed by the addition of DIPEA (88 mg, 0.66 mmol). The reaction mixture was stirred at room temperature for half an hour. Methyl 6-N-(methyl) aminohexanoate was added to this mixture dropwise and stirring was continued for 3 h. The reaction mixture was quenched with dilute HCl and extracted with 2:1 isopropanol-dichloromethane mixture. The organic layer was thoroughly washed with dilute HCl and brine, dried over Na$_2$SO$_4$, and concentrated under vacuum. The crude product was purified by flash column chromatography using 5 to 10% methanol in dichloromethane mixture.

Example 1

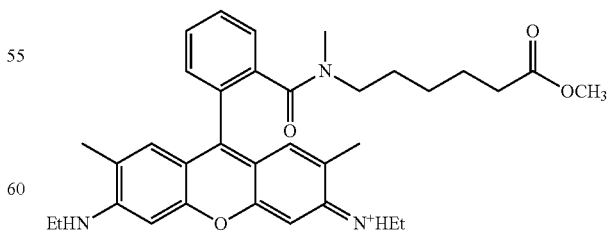

Rhodamine 6G-(6-carboxymethyl)-N-(methyl)-hexyl amide (d0) $^1$H NMR (400 MHz, CD$_3$OD): δ 1.05 (m, 4H), 1.44 (m, 8H), 2.1 (t, J=14 Hz, 2H), 2.17 (br s, 6H), 2.99 (s, 3H), 3.16 (t, J=13 Hz, 2H), 3.53 (q, J=13 Hz, 4H), 3.64 (s, 3H), 5.82 (t, J=8 Hz, 2H), 6.91 (s, 2H), 7.05 (s, 2H) 7.51 (m, 1H), 7.65 (m, 1H), 7.75 (m, 2H). M+ calcd 556.3175, found 556.3171.

Example 2

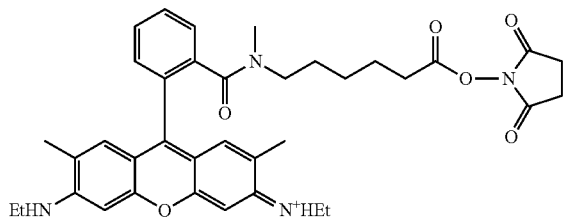

Rhodamine 6G-6-[carboxy-(N-hydroxysuccinimidyl)]-N-(methyl)-hexyl amide (d0): 1H NMR (CD₃OD): δ1.05 (m, 4H), 1.44 (m, 8H), 2.1 (t, J=14 Hz, 2H), 2.17 (br s, 6H), 2.67 (s, 4H), 2.99 (s, 3H), 3.16 (t, J=13 Hz, 2H), 3.53 (q, J=13 Hz, 4H), 5.82 (t, J=8 Hz, 2H), 6.91 (s, 2H), 7.05 (s, 2H) 7.51 (m, 1H), 7.65 (m, 1H), 7.75 (m, 2H). M+ calcd 639.3183, found 639.3194.

Example 3

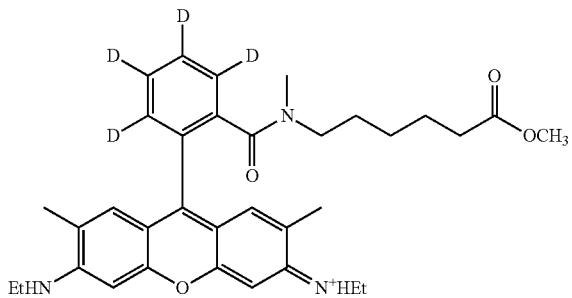

1H NMR (CD₃OD): δ 1.05 (m, 4H), 1.44 (m, 8H), 2.1 (t, J=14 Hz, 2H), 2.17 (br s, 6H), 2.99 (s, 3H), 3.16 (t, J=13 Hz, 2H), 3.53 (q, J=13 Hz, 4H), 3.64 (s, 3H), 5.82 (t, J=8 Hz, 2H), 6.91 (s, 2H), 7.05 (s, 2H). M+ calcd 560.3426, found 560.3420.

Example 4

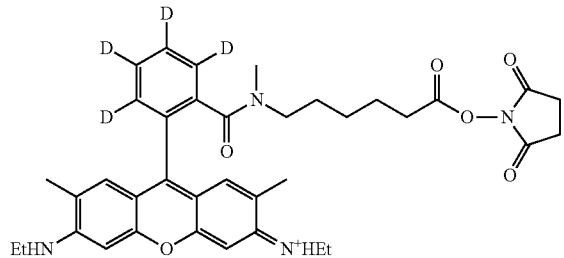

Rhodamine 6G-6-[carboxy-(N-hydroxysuccinimidyl)]-N-(methyl)-hexyl amide (d4): 1H NMR (CD₃OD): δ 1.05 (m, 4H), 1.44 (m, 8H), 2.1 (t, J=14 Hz, 2H), 2.17 (br s, 6H), 2.67 (s, 4H), 2.99 (s, 3H), 3.16 (t, J=13 Hz, 2H), 3.53 (q, J=13 Hz, 4H), 5.82 (t, J=8 Hz, 2H), 6.91 (s, 2H), 7.05 (s, 2H). M+ calcd 643.3433, found 643.3442.

Scheme 2 represents the synthesis of d2- and d6-R6G labeling reactive reagents. The d0- and d4-R6G free acid were dissolved into a mixture of CH3OD and a 35 wt % solution of deuterium chloride in deuterium oxide with a final acid concentration of 1 M. The solution was heated to 90° C. for two days in a closed vial. After the solution was cooled down to room temperature, it was concentrated under vacuum at 37° C. The mixture was dissolved in a 2:1 mixture of isopropanol and dichloromethane. The organic layer was washed twice with brine, dried with Na₂SO₄, and concentrated. The crude product was subjected to silica gel column chromatography to afford d2- and d6-R6G free acids, which were coupled to the linker, N-methylhexanylmethyl ester. The resulted methyl esters were hydrolysized under basic condition, and transformed by active NHS ester, N,N,N',N'-tetramethyl-O(N)-Succinimidyl)uranium tetrafluoroborate.

Scheme 2.

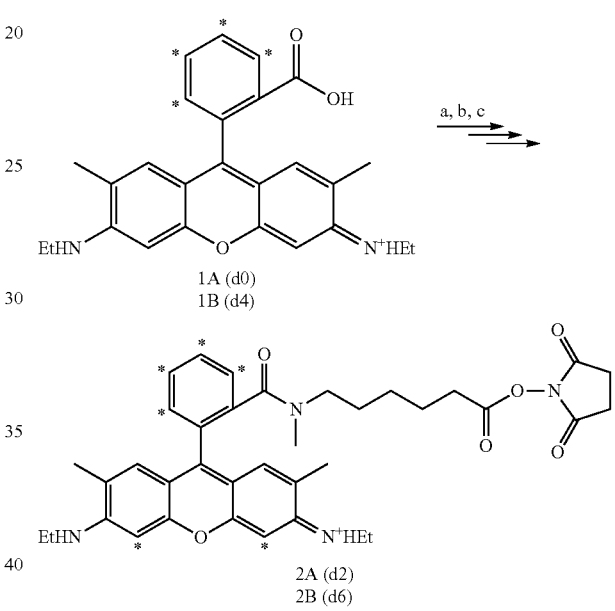

1A (d0)
1B (d4)

2A (d2)
2B (d6)

Reagents and conditions:
a DCl/D2O, 92-95%;
b HATU/DIPEA/NHMe(CH2)5CO2Me/DMF, 65-68%;
c Ba(OH)2/MeOH — H2O/Ac/CN/active MHS/,85-90%%. (active NHS = N,N,N',N'-tetramethy-O—(N-Succimidyl)uroniumdeuterium tetrafluoroborate).
The sites of deuteriumare noted with an asterisk.

Example 5

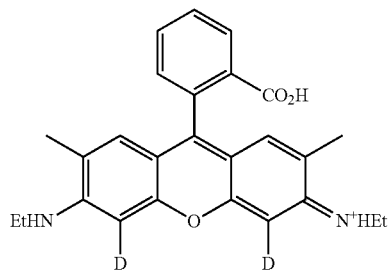

Rhodamine 6G-6-carboxylic acid (d2): 1H NMR (CD3OD) δ1.37 (t, 6H), 2.13 (br s, 6H), 3.62 (q, 2H), 6.86 (s, 1H), 6.92 (s, 1H), 7.51 (m, 1H), 7.65 (m, 1H), 7.75 (m, 2H). MS (ESI) calculated for C26H25D2N2O3 417.2147, found 417.2145.

Example 6

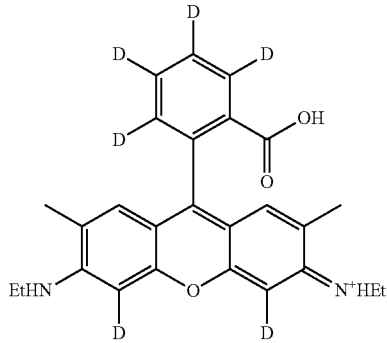

Rhodamine 6G-carboxylic acid (d6): 1H NMR (CD$_3$OD) 1.37 (t, 6H), 2.12 (br s, 6H), 3.58 (q, 2H), 6.85 (s, 1H), 6.92 (s, 1H). MS (ESI) calculated for C26H21D6N2O3 421.2398, found 421.2341.

Example 7

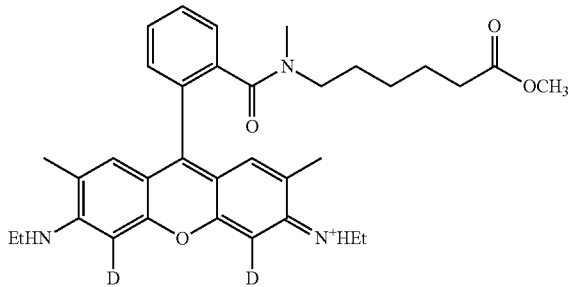

Rhodamine 6G-(6-carboxymethyl)-N-methyl)hexyl amide (d2): 1HNMR (CD$_3$OD), 1.06 (m, 4H), 1.44 (m, 8H), 2.1 (t, J=14 Hz, 2H), 2.17 (br, s, 6H), 2.99 (s, 3H), 3.16 (t, J=13 Hz, 2H), 3.53 (q, J=13 Hz, 4H), 3.64 (s, 3H), 5.82 (t, J=8 Hz, 2H), 6.85 (s, 1H), 6.91 (s, 1H), 7.51 (m, 1H), 7.65 (m, 1H), 7.75 (m, 2H). MS (ESI) calculated for C34H40D2N3O4 558.3301, found 558.3298.

Example 8

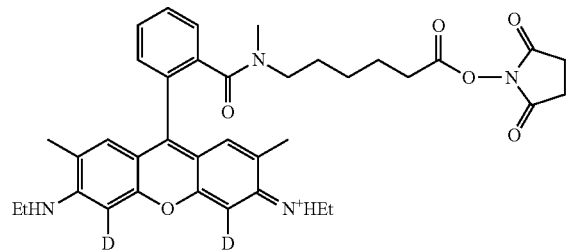

Rhodamine 6G-6-[carboxy-(N-hydroxysuccinimidyl)]-N-(methyl)-hexyl amide (d2): 1H NMR (CD3OD): 1.05 (m, 4H), 1.44 (m, 8H), 2.1 (t, J=14 Hz, 2H), 2.17 (br s, 6H), 2.67 (s, 4H), 2.99 (s, 3H), 3.16 (t, J=13 Hz, 2H), 3.63 (q, J=13 Hz, 4H), 5.82 (t, J=8 Hz, 2H), 6.86 (s, 1H), 6.91 (s, 1H), 7.51 (m, 1H), 7.65 (m, 1H), 7.75 (m, 2H). MS (ESI) calculated for C37H41D2N4O6 641.3308, found 641.3311.

Example 9

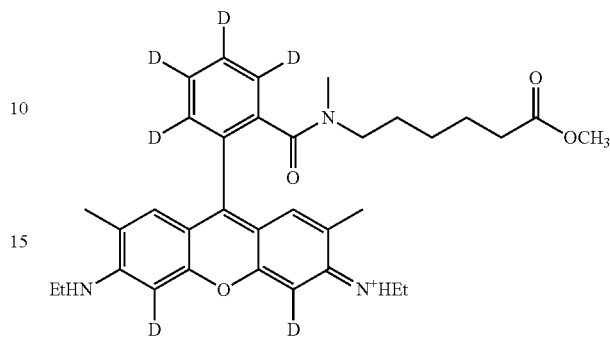

Rhodamine 6G-(6-carboxymethyl)-N-methyl)hexyl amide (d6): 1H NMR (CD3OD): 1.05 (m, 4H), 1.37 (t, 6H), 1.44 (m, 8H), 2.1 (t, J=14 Hz, 2H), 2.17 (br, s, 6H), 2.99 (s, 3H), 3.16 (t, J=13 Hz, 2H), 3.53 (q, J=13 Hz, 4H), 3.64 (s, 3H), 5.82 (t, J=8 Hz, 2H), 6.85 (s, 1H), 6.91 (s, 1H). M+ calculated for C34H36D6N3O4 562.3562, found 562.3566.

Example 10

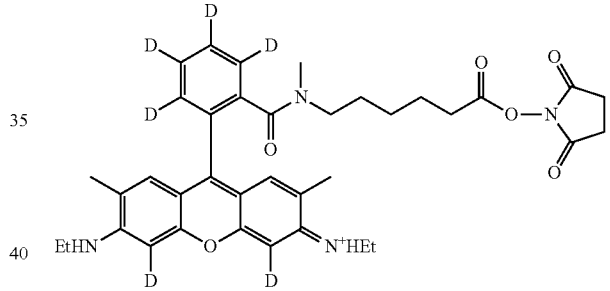

Rhodamine 6G-6-[carboxy-(N-hydroxysuccinimidyl)]-N-(methyl)-hexyl amide (d6): 1H NMR (CD3OD): 1.05 (m, 4H), 1.44 (m, 8H), 2.1 (t, J=14 Hz, 2H), 2.17 (br s, 6H), 2.67 (s, 4H), 2.99 (s, 3H), 3.16 (t, J=13 Hz, 2H), 3.53 (q, J=13 Hz, 4H), 5.82 (t, J=8 Hz, 2H), 6.86 (s, 1H), 6.91 (s, 1H). MS(ESI) calculated for C37H37D6N4O6 645.3559, found 645.3555.

Other Rhodamine 6G derivatives were produced from d5-toluene (with 5 deuterium substitutions). Nitration of toluene was obtained in very high yield with a mixture of trifluoromethanesulfonic acid, nitric acid, and sulfuric acid at low temperature. Treatment with ammonium sulfide provided regioselective reduction. The intermediate p-amino-nitrotoluene was purified by column separation. The amino group was then converted to hydroxyl group via diazotization followed by decomposition of the salt in aqueous sulfuric acid at elevated temperature. The nitro group on the 3-position was then reduced and alkylated to produce the deuterated 3-alkylamino-4-methylphenol. The deuterium atoms on the positions ortho to the phenyl group are very susceptible to hydrogen exchange reactions. However, at the end of the synthesis, hydrogen can be replaced with deuterium by treating the compound with a high temperature dilute acid (HTDA), such as deuterium chloride in deuterium oxide (DCl/D2O).

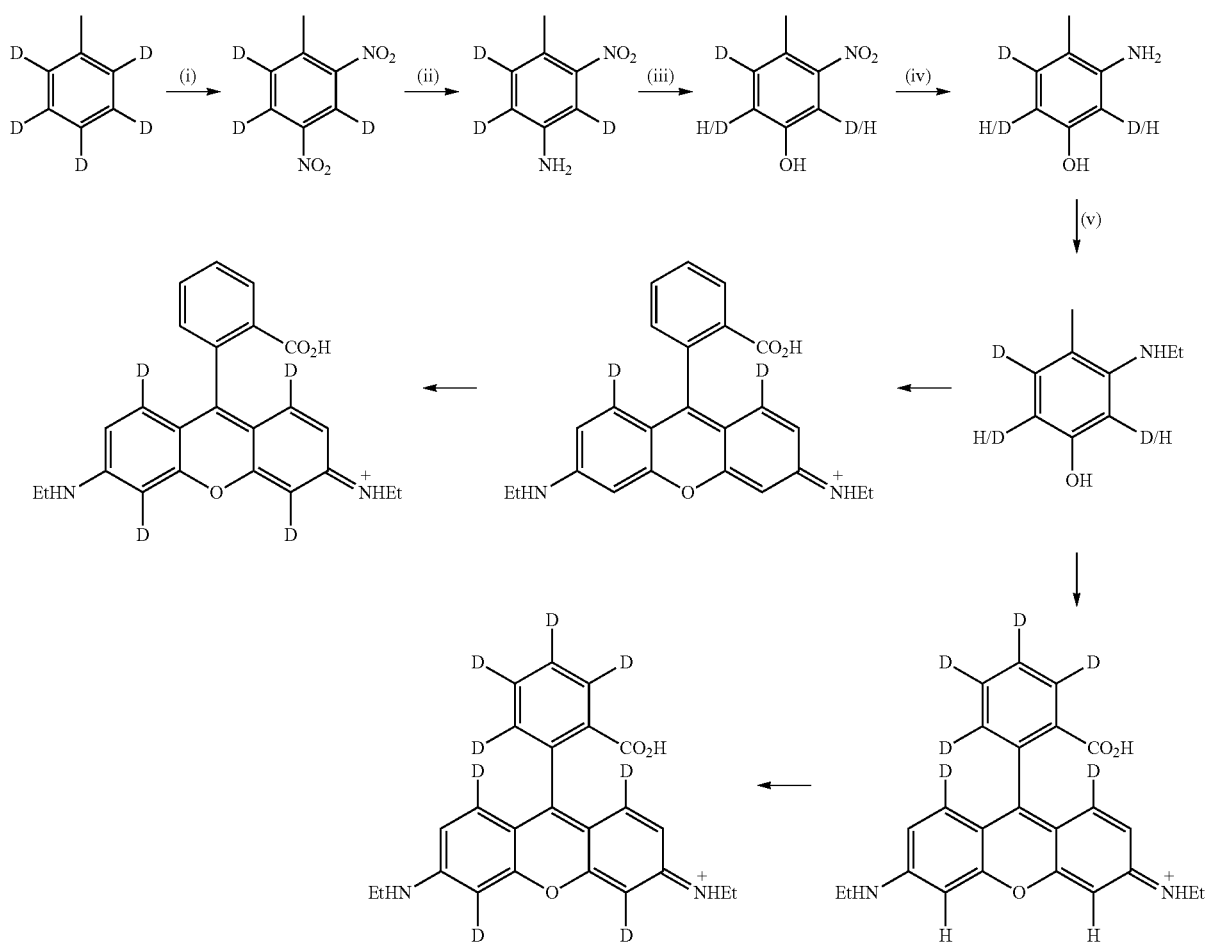

(i) CF$_3$SO$_3$H/HNO$_3$/H$_2$SO$_4$/-25° C.
(ii) (NH$_4$)$_2$S/H$_2$O/100° C./overnight
(iii) NaNO$_2$/H$_2$SO$_4$/0° C.; H$_2$SO$_4$/100° C.
(iv) Reduction
(v) NaBH$_4$/AcOH Synthesis of R6G-linker-sulfo-NHS ester to increase the water solubility of the conjugate. The following represents the synthesis of R6G-linker-sulfo-NHS ester.

Crystal violet labeling reagents were synthesized from aniline that reacted with (2-choloethyl)amine to afford 1-phenylpiperizine under basic condition. The secondary amine on the 1-phenylpiperizine was alkylated with methyl 6-bromohexanoate in the presence of sodium hydride. The resulting 4-ester substituted 1-phenylpiperizine reacted with bis(4-(dimethylamino)phenyl)-methanone under phosphoryl chloride in toluene to produce the precursor.

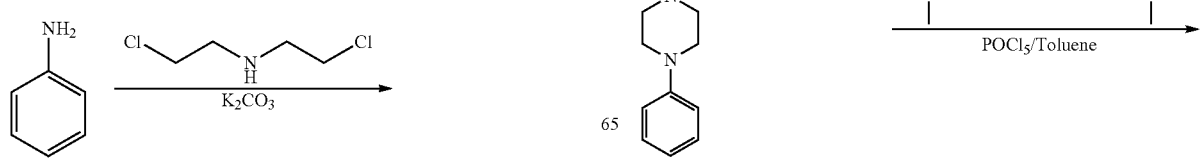

-continued

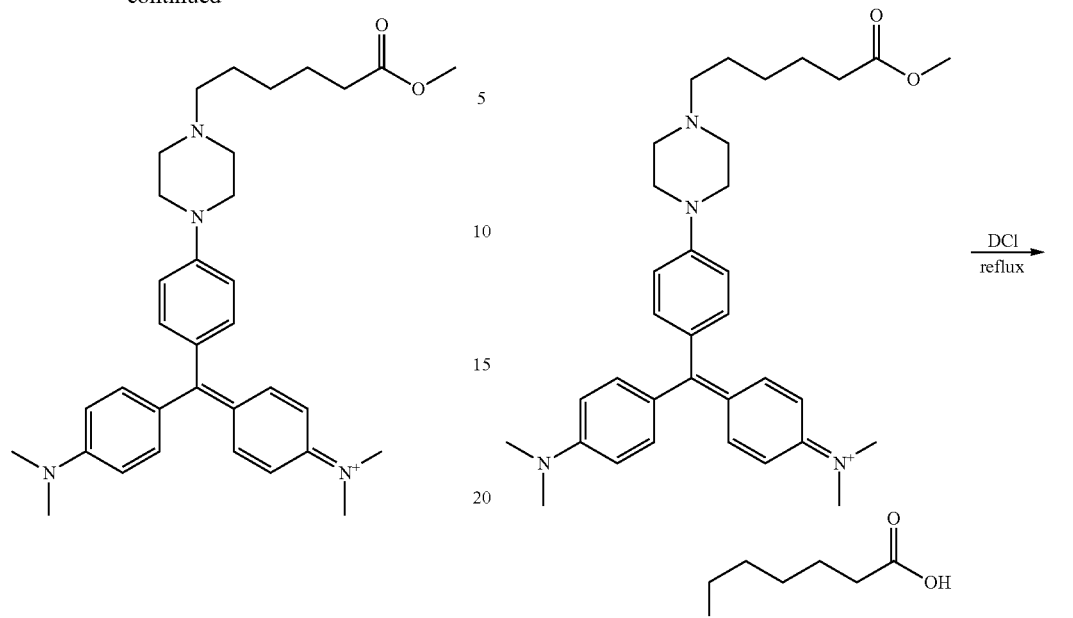

Example 12

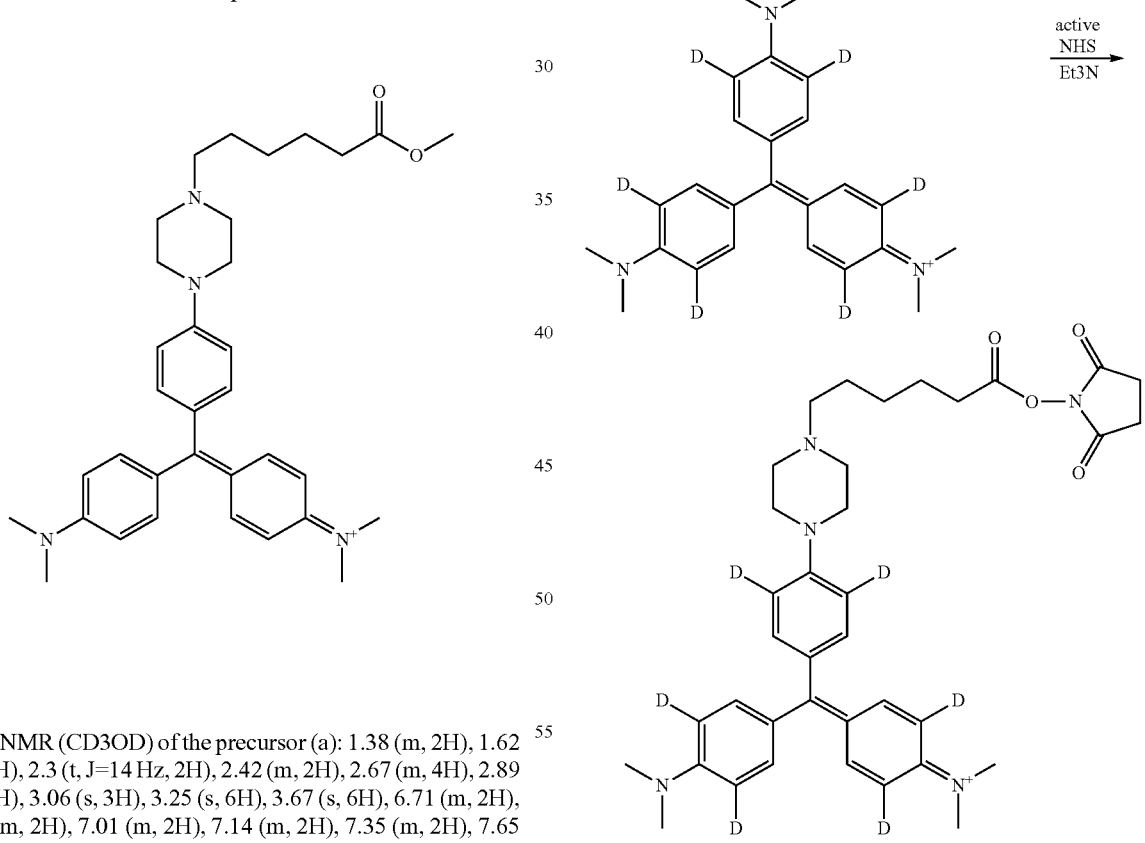

active NHS = N,N,N',N'-tetramethyl-O-(N-Succinimidyl)uronium tetrafluoroborate

¹H NMR (CD3OD) of the precursor (a): 1.38 (m, 2H), 1.62 (m, 4H), 2.3 (t, J=14 Hz, 2H), 2.42 (m, 2H), 2.67 (m, 4H), 2.89 (m, 4H), 3.06 (s, 3H), 3.25 (s, 6H), 3.67 (s, 6H), 6.71 (m, 2H), 6.89 (m, 2H), 7.01 (m, 2H), 7.14 (m, 2H), 7.35 (m, 2H), 7.65 (m, 2H). HRMS calculated for C34H45N4O2 541.3543, found 541.3547.

Synthesis of deuterated crystal violet labeling active reagents. The precursor was converted to the corresponding deuterated labeling reagents by hydrolyzed in DCl, then reacted with active NHS ester.

Other deuterated crystal violet labeling reagents were synthesized by the precursor d5-aniline. D5-aniline was reacted with (2-choloethyl)amine to afford 1-phenylpiperizine under basic condition. The secondary amine on the 1-phenylpiperizine was alkylated with methyl 6-bromohexanoate in the presence of sodium hydride. The resulting 4-ester substituted 1-phenylpiperizine reacted with bis(4-(dimethylamino)phenyl)-methanone under phosphoryl chloride in toluene to produce the deuterated precursor. D5-aniline was also reacted with Bis (trichloro)acetone to generate d10-bis(4-(dimethylamino)phenyl)-methanone, which was then reacted with d0- or d5-4-ester substituted 1-phenylpiperizine to produce the d8- or d12- precursors for labeling reagents synthesis, respectively. The d4- and d8 precursors were converted to d6 and d10 precursors in deuterium chloride.

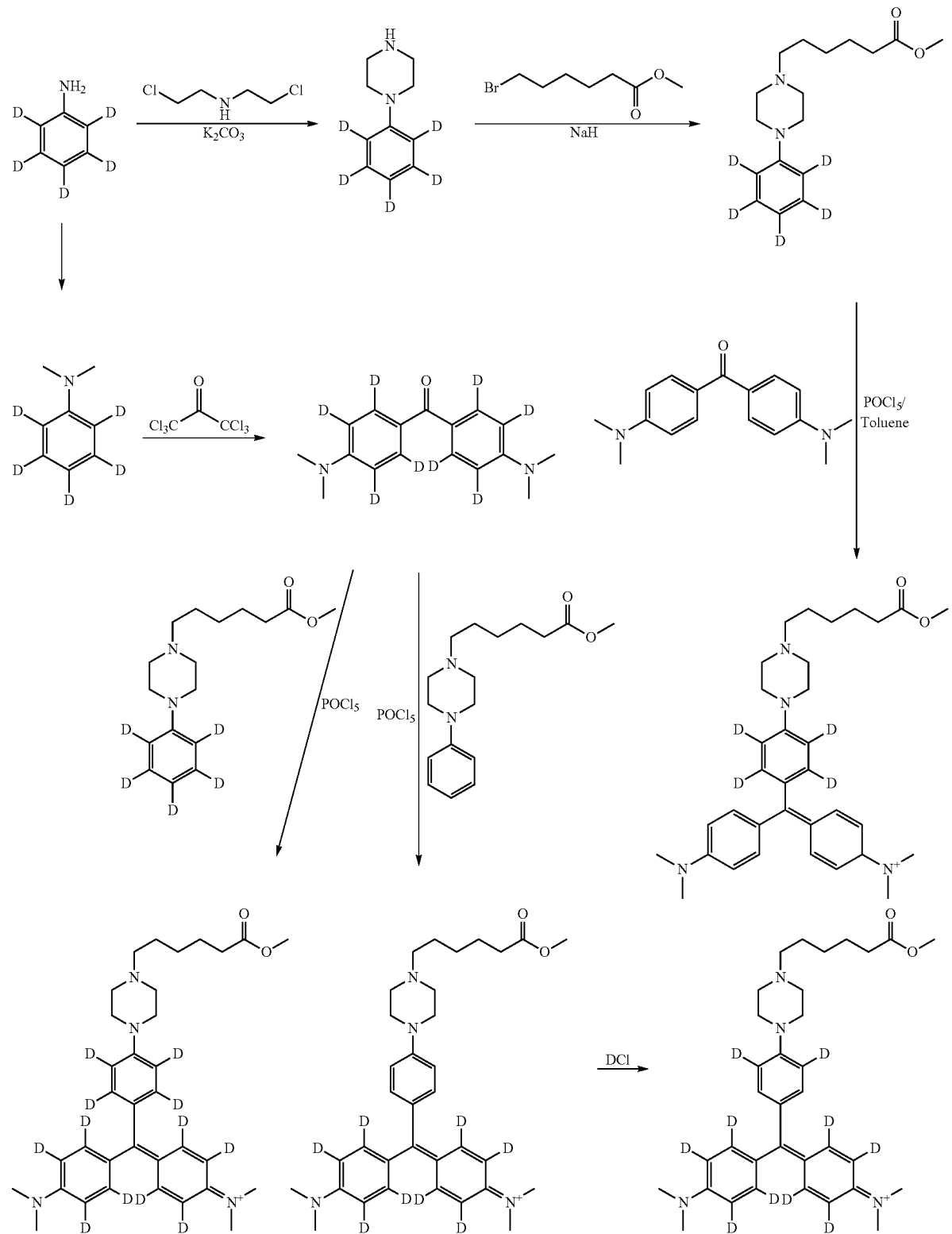

Phosphoramidite Analogs: The phosphoramidite functional group was coupled with the rhodamine and piperazine-crystal violet analogs using the methods known in the art (Scheme 3).

Scheme 3.

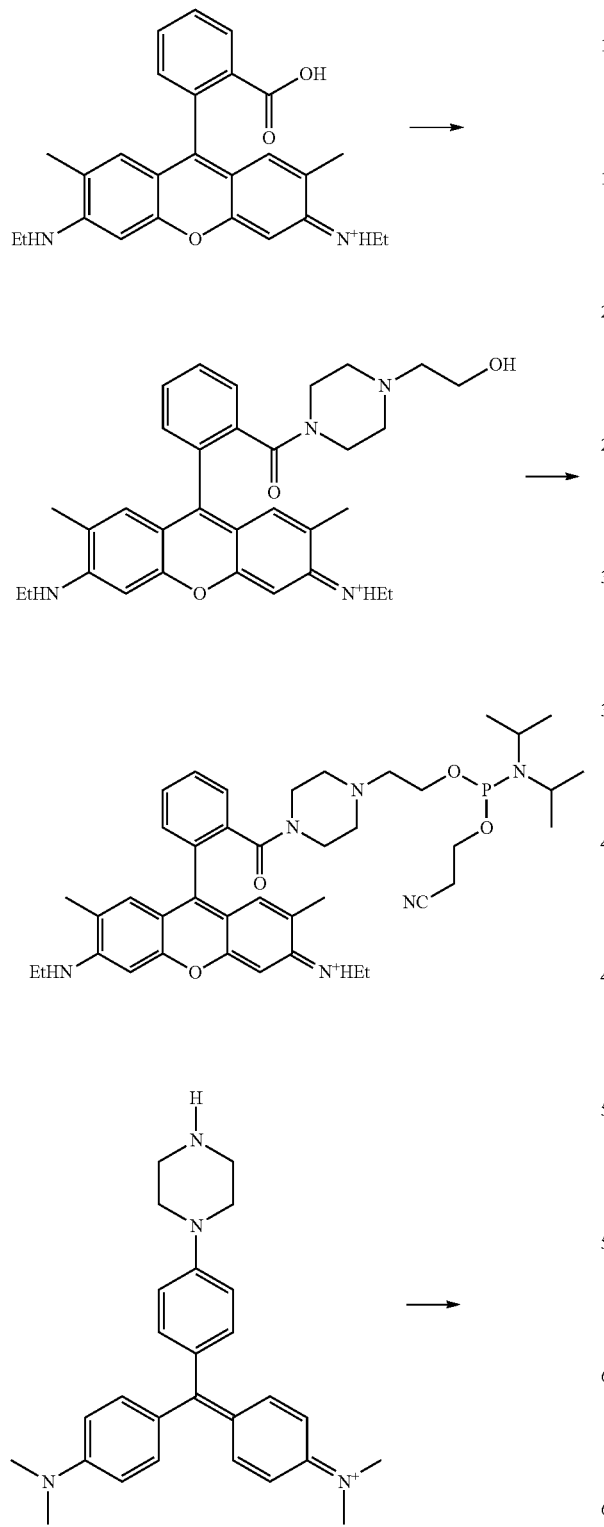

-continued

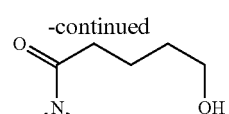

Quantification Methods

Example 1

Methodology for Quantitative SERRS Measurements

SERRS spectra. The SERRS spectra were acquired using a home-built 514 nm argon-ion micro-Raman system. The system utilized a 20× Olympus objective for scatter collection and coupled to a spectrograph (Acton, SpectraPro 300i, focal length=0.3 m, 1200 grids/mm) through a fiber bundle, and a liquid nitrogen cooled charge-coupled device (CCD, Princeton Instruments) was used for detection.

Silver Colloid Preparation. Silver colloid solution was prepared using an edited form of the Lee-Meisel citrate reduction of silver nitrate (P. C. Lee and D. Meisel, J. Phys. Chem. 86, 3391 (1982)). Twenty-five milligrams (25 mg) AgNO3 (>99%) was dissolved into 140 mL of high purity water (Millipore). The solution was brought to a boil with vigorous stirring before addition of 2.75 mL of 0.714% (w/w) lithium citrate and continued heating with stirring for 1 hour.

Measurement Protocol. All SERRS measurements were performed by mixing 2.20 mL of silver colloid solution, 2.20 mL of high purity water, and 50 μL of 2.25 M LiCl for aggregation in a 5 mL glass vial. A 45 μL aliquot of the analyte (dye) solution is added immediately following the aggregation as observed by the color change of the colloid from an olive green to a dark gray, giving a 100-fold dilution of the sample. Two separately prepared batches of silver colloid were used for all of the SERRS measurements described hereafter. The integration time per spectrum was 1 second unless otherwise noted.

Spectral Data Analysis. The SERRS spectra were analyzed using a least squares deconvolution method. The dye's d0:dx mixture spectra were deconvoluted into percentages of pure component spectra. The initial 50:50 mixture spectrum for each dye pair is used to rescale the pure component spectra to yield a perfect 50:50 deconvolution. The rescaled pure component spectra are used for the remaining ratios and replicate experiments for each dye pair (D. M. Zhang, Y. Xie, S. K. Deb, V. J. Davisson, and D. Ben-Amotz, Anal. Chem. 77, 3563 (2005)).

Non-isotopic SERRS Internal Standards.

Non-isotopic SERRS internal standards for concentration measurements were assessed. The spectra of rhodamine 19 perchlorate, rhodamine 101, and rhodamine 6G (R6G) shown in FIGS. 1A through 1C reveal significant spectral differences. However, the mixture spectrum (FIG. 1D) acquired for a 3:3:1 mixture of rhodamine-19:rhodamine-101:R6G (a ratio selected to compensate for the inherent differences in SERRS scattering efficiency of the dyes), reveals that the SERRS spectra of these dyes are not additive. This is most clearly observed by comparison with the spectrum in FIG. 1E, which is produced by mathematically adding the SERRS spectra of the three individual dyes (using the 3:3:1 weighting); the actual spectrum of the mixture in FIG. 1D bears limited resemblance to that expected for an ideally additive system. Further comparative analysis of the spectra for the pure dyes and that of the three-dye mixture indicated that the resulting spectra appear identical to that of only R6G.

Surface-Enhanced Resonance Raman Scattering Spectra of Deuterium Exchanged Dyes.

Figure 2:
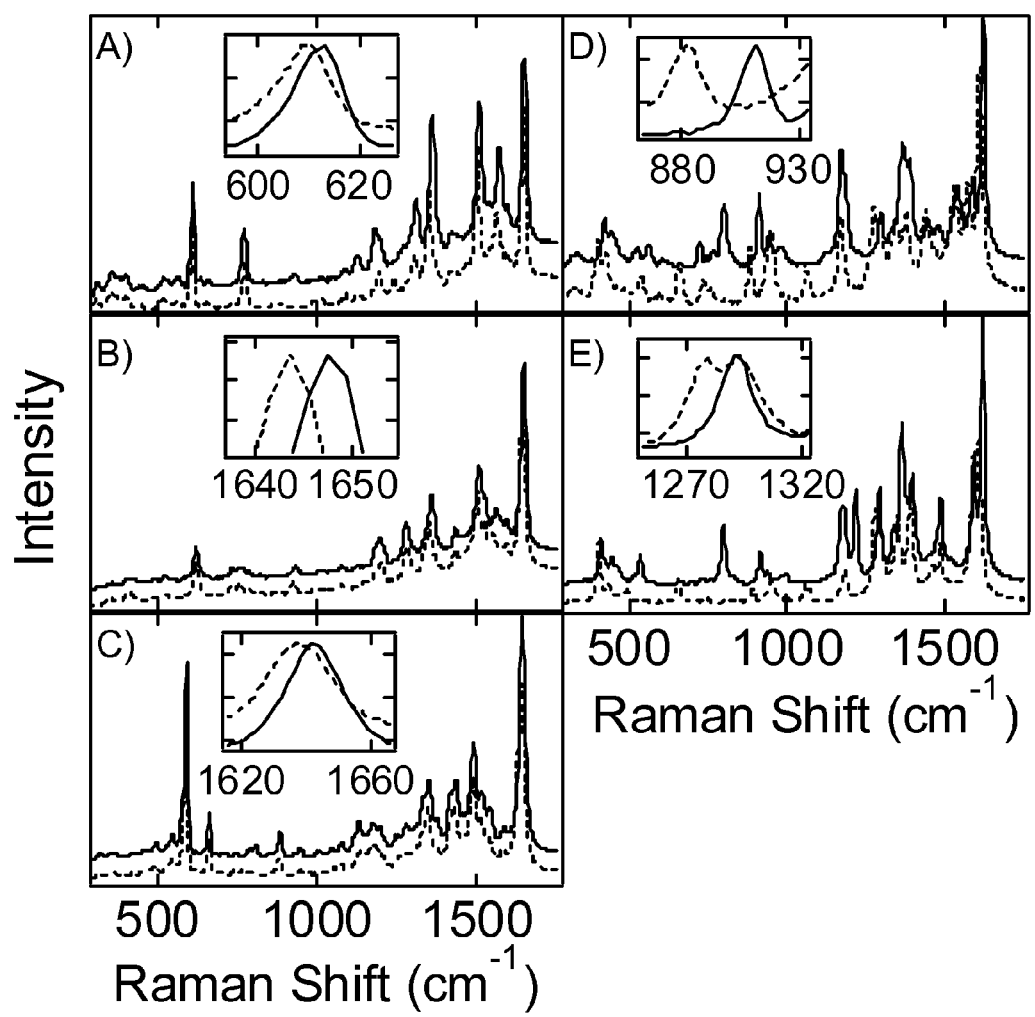
FIG. 2 is a graph of SERRS spectra. (A) 100 nM rhodamine 6G with no deuterium (R6G-d0), and rhodamine 6G with 2 deuterium substitutions (R6G-d2). (B) 100 nM rhodamine B d0/d2. (C) 1 μM nile blue d0/d2. (D) 100 nM crystal violet d0/d6. (E) 1 μM malachite green d0/d4. The insets in each plot show expanded views of the d0 peak (solid line) and the deuterium induced peak (dotted line) shift.

The SERRS spectra were obtained using a final concentration of 100 nM for R6G-d0/d2, rhodamine B-d0/d2, and crystal violet-d0/d6 and 1 µM for nile blue-d0/d2 and malachite green-d0/d4 (FIG. 2). The insets in each plot of dye pairs show an isotope-induced spectral difference that was used for relative concentration determinations. Each dye and the deuterium exchanged isotopomer display Raman signal shifts. For simplicity and clear demonstration of the quantitative capability of this method, only one peak shift was used in analyzing the spectra from solutions containing each isotopic dye pair. These peak changes were utilized for the quantitative analysis. The R6G-d0 peak at 613 cm$^{-1}$ for ring in-plane bending was shifted to 609 cm$^{-1}$ for R6G-d2 (FIG. 2A). Similarly, the rhodamine B -d0 peak of 1648 cm$^{-1}$ (C—C aromatic stretching) is shifted to 1644 cm$^{-1}$ for rhodamine B-d2 (FIG. 2B). The nile blue-d0 peak at 1642 cm$^{-1}$ (C—C aromatic stretching) is shifted to 1638 cm$^{-1}$ for nile blue-d2 (FIG. 2C). Crystal violet-d0 has a peak at 914 cm$^{-1}$ (ring skeletal vibration), which is shifted to 885 cm$^{-1}$ for crystal violet-d6 (FIG. 2D). The malachite green-0 peak at 1292 cm$^{-1}$ (ring C—C—H stretching) is shifted to 1278 cm$^{-1}$ for malachite green-d4 (FIG. 2E).

Quantitative Analysis with Isotopomers of Different Dye Classes.

The SERRS spectra of the five dye pairs, R6G-d0/d2, rhodamine B-d0/d2, nile blue-d0/d2, crystal violet-d0/d6, and malachite green-d0/d4, were measured and shown in FIG. 3. Five measurements were made for each dye pair mixture. Two batches of colloid were alternated through the five measurements; colloid batch one was used for measurements 1, 3, and 5 while colloid batch two was used for measurements 2 and 4 of the dye pair ratio experiments. The first set of measurements of all ratios for each dye was used as a training set for the remaining four sets of ratio measurements.

The mixtures of each dye (d0/dX) pair are at a constant total dye concentration but different relative dye concentrations. The spectral regions of interest of 578-637, 1605-1688, 1594-1711, 856-935, and 1243-1322 cm$^{-1}$ for R6G-d0/d2, rhodamine B-d0/d2, nile blue-d0/d2, crystal violet-d0/d6, and malachite green-d0/d4, were zoomed-in, respectively. Each dye pair plot contains the spectra, (a)-(g), of the dye pair's d0/dX ratio of 100/0, 75/25, 67/33, 50/50, 33/67, 25/75, 0/100, all at a constant total dye concentration of 100 nM for R6G-d0/d2, rhodamine B-d0/d2, and crystal violet-d0/d6 and 1 µM for nile blue-d0/d2 and malachite green-d0/d4.

Spectral decomposition of the SERRS spectra was performed by first truncating each spectrum to the wavenumber window specified for each dye pair. A baseline correction was then performed by fitting the first three and last three data points of each truncated spectra to a line before subtracting this baseline from the truncated spectra. The seven baseline corrected and truncated spectra of solutions with seven different dye concentration ratios constitute the data matrix D. The same correction procedure is followed to produce the pure spectra matrix S containing baseline corrected and truncated pure component spectra. The decomposition for a set of d0:dx ratio mixtures was performed by using least squares decomposition to generate a matrix C that contains the relative amounts of the pure spectra, S1 and S2, in each of the ratio spectra contained in D (D. M. Zhang, Y. Xie, S. K. Deb, V. J. Davisson, and D. Ben-Amotz, Anal. Chem. 77, 3563 (2005)).

For each dye class, the pure spectra S1 and S2 were intensity adjusted to generate a C1/C2 ratio of 1 for the 50/50 mixture in the first set of measurements. The intensity-adjusted S1 and S2 pairs were used to create the matrix S in the remaining four sets of ratio measurements for that dye pair. The FIG. 3 insets show the average measured percentage of the deuterium-labeled component of each dye pair versus the actual percentage.

The average prediction errors for the dye pairs were 1.5%, 1.2%, 1.1%, 2.2%, and 1.1% for R6G-d0/d2, rhodamine B-d0/d2, nile blue-d0/d2, crystal violet-d0/d6, and malachite green-d0/d4, respectively. The detection limits for the dyes in this study varied from species to species. R6G had a lower detection limit than the other four dyes when using excitation at 514 nm. Higher concentrations of these dyes were restricted due to the short wavelength excitation producing significant fluorescence when used with samples with a greater concentration than 1 µM.

Example 2

Detection and Relative Quantification of Proteins

Labeling and Purification of Model Proteins. Protein labeling was carried out under conditions for comparable reagents (e.g. TAMRA or fluorescein-NHS tagging reagent from Pierce) at the 200 nmol per milligram protein scale (Geoghegan, 1996). Labeling efficiency of the d0 and d4-R6G-NHS reagents was tested across a set of standard proteins including: bovine β-casein, human erythrocyte carbonic anhydrase I, bovine serum albumin, bovine catalase, rabbit muscle glycogen phosphorylase, bovine lactoperoxidase, bovine pancreatic RNase A, horse heart cytochrome c, equine ferritin, and chicken lysozyme (Sigma or Amersham-Pharmacia). The extent of dye incorporation per protein molecule was determined by UV-Vis spectroscopy, using extinction coefficients ε (540 nm)=116,000 M$^{-1}$cm$^{-1}$ for R6G and E (280 nm) for protein calculated from amino acid sequence composition of these proteins (Gill & von Hippie, 1989). Using the 200 nmol/mg scale reaction resulted in an average molar incorporation ratio of 5 moles dye per mole protein (but ranged from 0.1 to 10 dye/protein across the different proteins). There was no difference between the reaction efficiencies of the isotopomeric forms of the R6G-NHS reagents.

Labeling Protocol. Labeling of purified protein samples was carried out as follows. One mg of protein was prepared in 100-200 µl of 50 mM borate buffer, pH 8.5, to which was added 200 nmol of either d0 or d4-R6G-NHS reagent dissolved in 5 µl DMF. The molar ratio of dye to protein 4:1. After 1 hour incubation in the dark at room temperature, the labeling reaction was desalted on a PD-10 column (GE Healthsciences) into 50 mM HEPES pH 7.5. The desalted protein was then concentrated and buffer exchanged with 8 M urea, 10 mM HEPES pH 7.5, and 0.5% CHAPS on a 5,000 MW cutoff Microspin filter (Millipore), to remove any remaining nonreacted dye. Samples were stored at −80° C. for later analysis.

SDS-PAGE and Silver Stain Procedure. Proteins were loaded onto 4-20% TRIS-glycine gels (Cambrex) with 20 pmol of dye per lane, at the following d0:d4 ratios: 20:0, 18:2, 15:5, 10:10, 5:15, 2:18, and 0:20. After the gels were completed, silver deposition for SERRS imaging was accomplished using the following silver stain method. The gels were fixed in 50% methanol, 5% acetic acid (1 h), and then washed with 50% methanol (20 min), and water (10 min). The protein gels were reduced using 1.25 mM sodium thiosulfate ($Na_2S_2O_3$, 2 min), then stained in 0.1% silver nitrate (20 min), and developed in 2% sodium carbonate solution containing 0.04% formaldehyde until the protein bands are visible (~5 min). Darkest silver staining occurred in bands containing 1-5 µg protein, and faint but distinct staining was observed in 0.2 µg protein bands. The development step is subjective, but was quenched when the contrast between protein bands and empty gel regions no longer improved and before the most intense protein spots become "mirrored". Development was quenched quickly by decanting of the formaldehyde solution and replacement with 5% acetic acid solution for 5 min. Gels were imaged immediately by SERRS, and stored at 4° C. in water for up to 1 month.

SERRS Imaging. Raman imaging was performed on a custom built micro-Raman system, equipped with an air-cooled 514.5 nm $Ar^+$ laser (Melles-Griot) that was directly coupled to an Olympus BX41 microscope. Raman scatter was collected using an Olympus 20X objective and focused onto a circular-to-linear fiber bundle for detection using a Spectra-Pro 300i spectrograph (Acton Research) and a 1024X256 LN-cooled CCD (Princeton Instruments) (Xie et al, 2005). Gel imaging was performed using a custom written LabVIEW (National Instruments) program which raster scans the gel through the laser focus while collecting a full spectrum from each imaging point. The laser focal spot size is 10 µm in diameter, and the x-y step size in fluorescence or Raman scatter images was 200 or 250 µm. Gels were placed on a low fluorescence glass plate (Bio-Rad) under a small pool of Milli-Q to prevent drying over the duration of the scan. SERRS imaging parameters using this system were: laser power, 14 mW at sample; spectrograph, 1200BLZ at 554 nm; exposure time, 1 sec. At 100 µm step size, and 1 ms spectrum scans require 10 s per $cm^2$ of gel area, and roughly 20 min for each gel.

Ferritin samples labeled with d0- or d4-R6G were mixed in varied ratios and separated on SDS PAGE. Referring to FIG. 4, the protein bands were imaged first by fluorescence, followed by silver staining and SERRS spectral imaging again. The spectral shifts at 600 $cm^{-1}$ were used to calculate the percent isotopic compositions for d0 and d4 R6G corresponding to the relative amounts of the two ferritin samples. The SERRS spectral signature reflects that of the isotopomeric label as shown (FIG. 4E). The expected statistical distribution of the two labeled proteins in the PAGE gel format was observed.

Example 3

Quantification of Proteins in 2-D Gels

Materials. All 2-DGE materials were from Biorad. Recombinant human GMP synthetase (hGMPS) was produced by Oliver, J. C., with purity of >95% (Oliver, J. C. (2006), Ph.D. Thesis, Purdue University, West Lafayette, Ind., 173 p). All other reagents were purchased from Sigma.

Soluble Cell Lysate Preparation. HCT116 colon cancer cells (ATCC) were cultured using standard cell culture conditions in DMEM-F12 medium containing 10% FBS. Cells were harvested by trypsin release, then rinsed three times with PBS, and pelleted for storage at −80° C. For lysis, thawed cell pellets were suspended in chilled lysis buffer containing 20 mM HEPES, pH 7.5, 0.25 M sucrose, 3 mM $MgCl_2$, 0.5% NP40, 2 mM DTT, and 1× Halt protease inhibitor cocktail (EDTA-free, Pierce). The cells ($2 \times 10^7$ cells/mL) were homogenized with fifteen strokes of a 2 mL Dounce homogenizer and pestle B, and then cellular debris was pelleted at 12 000 g for 20 min at 4° C. The supernatant was concentrated and buffer exchanged into 50 mM borate buffer pH 8.5 using 5 kDa MW cutoff ultrafree spin filters (Millipore), and the protein concentration was determined using the Biorad protein assay with BSA calibration. Prepared lysates were used immediately for labeling and 2-DGE analysis.

Protein Labeling. For lysate or recombinant protein sample labeling, 100-150 µg of protein was dissolved in 50 mM borate buffer pH 8.5 to a final volume of 200-1200 µL, to which was added 1 nmol (1 µL) of d0- or d4-R6G-NHS reagent stock dissolved in ethanol. After 1 hour incubation in the dark at room temperature, the protein reaction was desalted on a PD-10 column (GE Healthsciences) into 50 mM Tris pH 7.5 buffer. The total protein eluate was concentrated then buffer exchanged with 8 M urea, 10 mM Tris pH 7.5, and 0.5% CHAPS on a 5 k MW cutoff microspin filter, to remove any remaining unreacted dye. Protein concentration was determined using the Biorad protein assay, and dye content was assessed by UV-vis absorbance using c=116 000 $M^{-1}cm^{-1}$ at $\lambda_{max}$ of 540 nm for R6G. These reaction conditions produced a low molar labeling efficiency (about 0.1%), and were optimized using controlled mixtures of proteins with known pI and Mw and various dye/protein reaction stoichiometry, selecting for conditions that produced unaltered 2DGE images between labeled vs unlabeled samples (Loethen, Y. L., Knudsen, G. M., Davis, B., Gudihal, R., Davisson, V. J., and Ben-Amotz, D. (2008), J. Proteome Res. 7, 1341-1345).

2D-PAGE. For isoelectric focusing, protein in a volume of less than 20 µL was diluted into sample rehydration buffer containing 8 M urea, 2% CHAPS, 50 mM DTT, 0.2% Bio-Lyte 3/10 ampholyte, and 0.001% bromophenol blue for rehydration of 11 cm, 3-10 nonlinear IPG strips. The IEF strips were focused under optimized conditions for mammalian cell lysates (Leimgruber, R. M., Malone, J. P., Radabaugh, M. R., LaPorte, M. L., Violand, B. N., and Monahan, J. B. (2002) Proteomics 2, 135-144.) over 16-20 hours for a total of about 60 000 Vh using a shallow gradient over five voltage steps, reaching a maximum of 8000 V on a Biorad Protean IEF Cell apparatus. After focusing, the strips were reduced and alkylated in equilibration buffer containing 6 M urea, 0.375 M Tris pH 8.8, 4% SDS, 20% glycerol containing 2% DTT for 10 min, then 2.5% iodoacetamide for 10 min. For the second dimension, the strips were run on single well, precast, Criterion 12.5% acrylamide Tris-HCl gels. The gels were fixed in 50% methanol, 5% acetic acid for 1-2 h, followed by 50% methanol 1 hour, then stored in water at 4° C. Gels of non-R6G-labeled control protein samples were stained with SyproRuby according to the manufacturer protocol (Biorad).

Fluorescence Scanner Gel Documentation. Fluorescence images of 2D gels were recorded using a Typhoon fluorescence scanner (GE Life Sciences), with the following settings for R6G: 532 nm excitation, 580 (±30) nm bandpass emission filter, and 100 µm pixel size; and the photomultiplier voltage was adjusted for maximum dynamic range of signal, typically 650 V. For SyproRuby detection, 532 nm excitation and the 610 (±30) nm bandpass emission filters were used.

Silver Staining. Polyacrylamide gels were silver stained according to the Schevchenko method with modifications to minimize background staining (Mortz, E., Krogh, T. N., Vorum, H., and Gorg, A. (2001), Proteomics 1, 1359-1363; Shevchenko, A., Wilm, M., Vorm, O., and Mann, M. (1996), Anal. Chem. 68, 850-858). The gels were reduced for 2 min in freshly prepared 2 mM sodium thiosulfate ($Na_2S_2O_3$). Then, the gels were rinsed twice in water over 5 min before incubation in chilled (4° C.) 0.1% silver nitrate solution for 20 min. The gels were then rinsed with two exchanges of water over 4 min, and then incubated in 10% sodium carbonate containing 0.04% formaldehyde until the protein spots had developed sufficient brown staining for visualization. Development was quenched before the appearance of excessive mirroring with a 2 min wash in 5% acetic acid. Where indicated, gels were preserved by soaking in 10% glycerol and drying between sheets of cellophane at room temperature.

d0/d4-R6G Ratiometric Accuracy. The practical limits of the ratiometric quantification strategy were assessed using mixtures of separately labeled d0- or d4-R6G-recombinant hGMPS. Gel-to-gel reproducibility and precision were assessed for a 43% d4-R6G composition sample, representing a 1.3-fold difference between d0- and d4-R6G concentrations. Three replicate gels containing 3 µg total of the mixed protein sample were separated by 2-DGE, silver stained, and then dried as described above. A practical detection limit was determined by sampling a series of 2-DGE samples containing 3 µg, 300 ng, 30 ng, or 3 ng total hGMPS protein. The sample composition was selected to be 64.2% d0-R6G, representing a 1.8-fold difference between d0- and d4-R6G samples, a value selected to be significant at picomolar R6G concentrations. For these samples, a single-point determination procedure was followed using a Senterra confocal Raman microscope (Bruker Optics) operated with Opus v 6 software. The Senterra was equipped with a 532 nm laser and Olympus MPlan 20×(0.4 NA) or 50×(0.75 NA) objectives, with collection spot size dimensions of 50×1000 µm, and 3-5 $cm^{-1}$ resolution grating settings. The following settings were used to acquire spectra for 0.1-1 µg protein: 2 mW power, 2-5 scans, 30 s integration time; and for 1-10 ng protein: 5-10 mW, 5 scans, and 60 s integration. Data were fit using a manual curve fitting operation within Opus software around the signature 610 and 600 cm-1 peaks, using baseline subtraction between 619 and 587 $cm^{-1}$, and a Gaussian peak shape model. The ratio of areas of the 610 to 600 $cm^{-1}$ peaks directly provided values of d0/d4 composition.

d0/d4-R6G-Labeled Spiked Lysate. To produce spiked lysate samples, HCT116 cell lysate was divided equally into three vials containing 750 µg lysate, to which was added 0, 1.5, or 3 µg of recombinant hGMPS. These samples were labeled in separate reactions to give two d0-lysates containing w/w 0% or 0.2% spiked recombinant hGMPS and a single d4-lysate containing 0.4% spiked recombinant hGMPS. Mixed composition d0/d4 samples were combined as follows: Sample A: 100 µg each of the 0-labeled, 0% spiked, and d4-labeled, 0.4% recombinant hGMPS-spiked lysates. Sample B: 100 µg each of the d0-labeled, 0.2% spiked, and d4-labeled, 0.4% spiked lysates. The d0-R6G labeled, non-spiked lysate sample was also used as a control (Sample C).

Theoretical Percent d4-R6G Composition in Spiked Lysates. The theoretical percent d4-R6G composition in a given hGMPS protein spot was calculated as a function of the composition of endogenous hGMPS and the recombinant protein that was added to it. For each protein spot, endogenous (E) protein was defined as the mass (ng) of hGMPS present in 200 µg of cell-free lysate. The mass of recombinant (R) protein (ng) in a protein spot was calculated per 200 ng recombinant protein (or 0.1% w/w addition of recombinant protein to 200 µg of lysate). The theoretical composition of d4-R6G (%) in samples A and B was then given by equations 1 and 2.

$$\% \; d_4(\text{sample } A) = \frac{\left(\frac{E}{2} + 2R\right)}{(E + 2R)} \quad (1)$$

$$\% \; d_4(\text{sample } B) = \frac{\left(\frac{E}{2} + 2R\right)}{(E + 3R)} \quad (2)$$

Multispectral Fluorescence and Raman Imaging. Full spectral imaging was performed using a custom-built micro-Raman system (Xie, Y., Jiang, Y., and Ben-Amotz, D. (2005), Anal. Biochem. 343, 223-230), equipped with an air-cooled 514.5 nm $Ar^+$ laser (Melles-Griot) and an Olympus BX41 microscope. Raman scatter was collected using a 20× objective (Olympus ULWD MSPlan, 0.4 NA) and focused onto a circular-to-linear fiber bundle for detection using an imaging spectrograph (Acton Research, SpectraPro 300i) and a 1024× 256 LN-cooled CCD (Princeton Instruments). Gel imaging was performed using a custom-written LabVIEW (National Instruments) program to raster scan the gel through the laser focus while collecting spectra from an array of points in the gel. The laser focal spot size was 10 µm in diameter and 100 µm in depth, effectively 10 pL focal volume, and the x-y step size in fluorescence or Raman scatter images was 200 or 250 µm. Gels were placed on a low-fluorescence glass plate (Bio-Rad) under a small pool of Milli-Q water to prevent drying over the duration of the scan. Fluorescence imaging parameters were as follows: laser power, 1 mW at the sample; spectrograph grating, 300BLZ at 670 nm; exposure time, 5 ms; image size, about 70×40 pixels=17.5×10 mm; scan time=10 min. SERRS imaging parameters were as follows: laser power, 14 mW at sample; spectrograph grating, 1200BLZ at 554 nm; exposure time, 1 s; image size, about 48×48 pixels=12×12 mm; scan time, 1 h.

Analysis of Multispectral Fluorescence and Raman Imaging. Absolute Dye Quantification by Fluorescence. For absolute R6G quantification in protein spots, the water-Raman subtraction method (WIS) of Loethen et al. (Loethen, Y. L., Knudsen, G. M., Davis, B., Gudihal, R., Davisson, V. J., and Ben-Amotz, D. (2008) J. Proteome Res. 7, 1341-1345) was applied to a small region of the gel containing the spiked sample. Calibration of dye concentration in solution was performed using d0-R6G and an additional region was imaged from the gel margin (protein-free) for calculating an average spectrum to be used as background. Savitzky-Golay second derivative solvent subtraction analysis of all spectra yielded the normalized value of R6G fluorescence to the water Raman band (Loethen, Y. L., Zhang, D., Favors, R. N., Basiaga, S. B. G., and Ben-Amotz, D. (2004), Appl. Spectrosc., 58, 272-278; Savitzky, A., and Golay, M. J. E. (1964), Anal. Chem. 36, 1627-1639). Dye concentration was calculated over the volume of a protein spot using the protein-free R6G calibration and the normalized fluorescence spectral integration obtained from each image pixel. Using this method, a user-defined protein spot was selected as an internal standard for which the absolute molar amount of dye was quantified. The relative fluorescence in this spot was used to normalize signal across replicate fluorescence gel images.

Automated SERRS Spectral Processing. To remove the fluorescence background from SERRS spectra, an automated method of polynomial fitting was used to model a composite fluorescence spectrum that could be subtracted (Lieber, C. A., and Mahadevan-Jansen, A. (2003), Appl. Spectrosc. 57, 1363-1367). This procedure involved pixel by pixel comparison of the original spectra with a fourth-order polynomial fit and generating a composite spectrum by inputting the lesser of the original spectrum pixel value or the polynomial pixel value. Five or more iterations were performed to arrive at a composite spectrum that contained few or no Raman bands, smoothed using a second-order Savitsky-Golay width of 25 pixels (Savitzky, A., and Golay, M. J. E. (1964), Anal. Chem. 36, 1627-1639), and subtracted from the original spectrum yielding a nearly null baseline SERRS spectrum.

Partial least-squares (PLS) modeling was used to quantify d0- and d4-R6G composition, using full-range, baseline subtracted, second-derivative SERRS spectra. To generate the PLS model, a training set was collected with 200 spectra obtained for each of the following % d4-R6G compositions: 100%, 75%, 50%, 25%, or 0% of a standard, d0- or d4-R6Glabeled purified protein (ferritin), as described in example 5 and J. Am. Chem. Soc. 130, 9624-9625 (Deb, S. K., et. al, (2008)). These spectra were weighted by standard deviation over the 200 spectra for each set, but otherwise were not manipulated for this analysis. The final calibration plots for PLS modeled training set data with observed versus expected % d4-R6G composition had a linear R2 correlation coefficient of 0.999.

Quantitative Fluorescence and Raman Imaging.

Figure 5A:
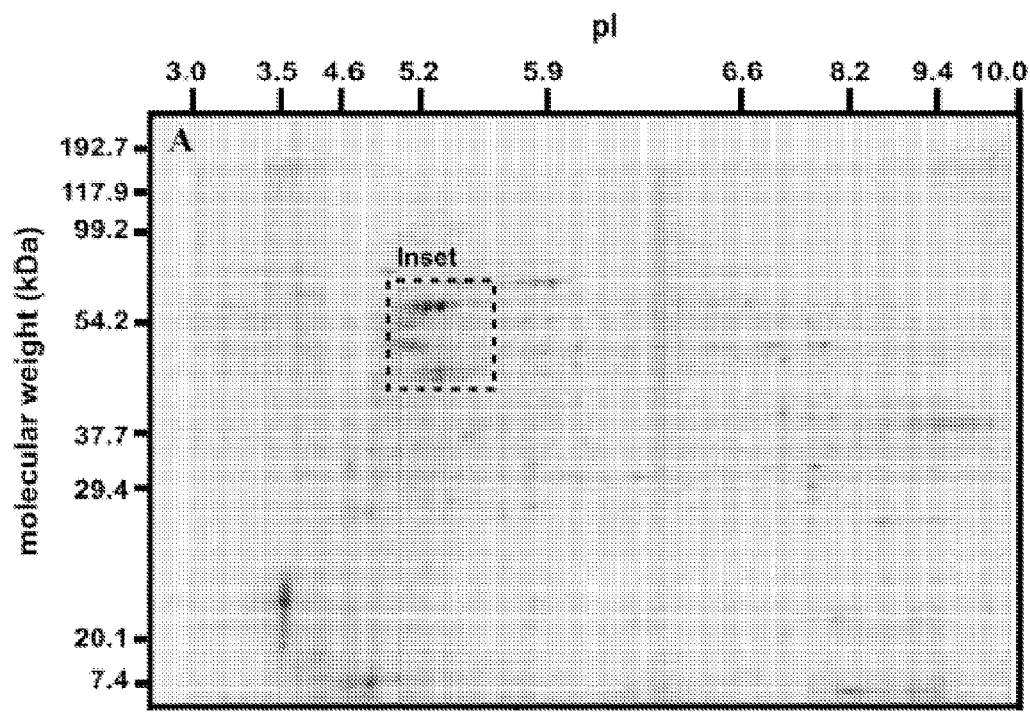
FIG. 5 illustrates a 2-DGE analysis of 30 μg of R6G-labeled lysate. (A) The full-sized fluorescence image was recorded with a Typhoon fluorescence scanner. (B) The 13×13 mm$^2$ inset region was further imaged on a custom-built confocal fluorescence system (200 μm step size). (C) Representative fluorescence spectra are shown for protein (on the ×10$^3$ scale), background (on the 1× scale), and water-subtracted background (on 1× scale). (D) The gel was stained with silver, then imaged by Raman in the same inset region, color coded for intensity at 1650 cm$^{-1}$ from red (high) to blue (low). (E) A representative background-subtracted SERRS spectrum from the marked protein spot is shown.
Figure 5B:
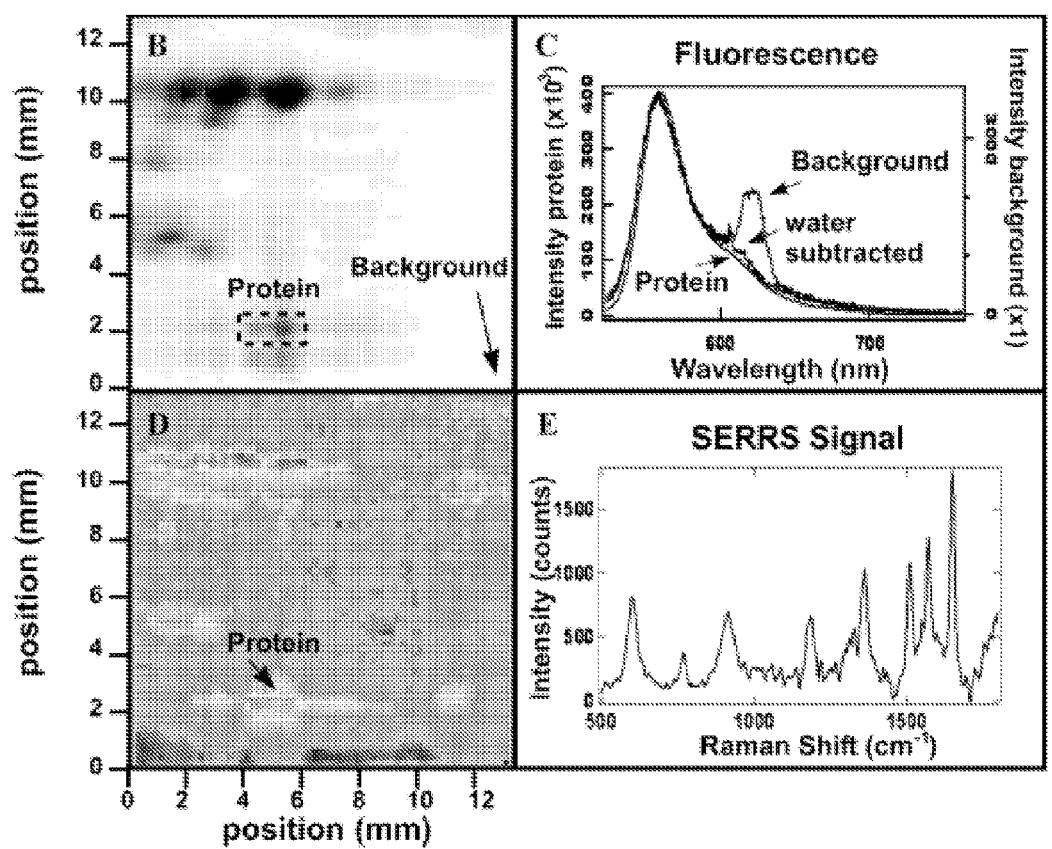

A 30 µg soluble lysate sample was labeled using R6G-NHS ester lysine labeling reagent at a ratio of 6.6 pmol dye per microgram protein to yield on average about 0.1% labeling efficiency. The sample then was subjected to 2-DGE separation, fluorescence spectral imaging, silver nanoparticle deposition, and Raman spectral imaging. The absolute dye content in a single protein spot on the 2D gel was established using a water internal standardization method that compares the fluorescence of R6G to the water Raman signal (Loethen, Y. L., Knudsen, G. M., Davis, B., Gudihal, R., Davisson, V. J., and Ben-Amotz, D. (2008), J. Proteome Res. 7, 1341-1345). The corrected spectra for the R6G fluorescence intensity image is shown in FIG. 5B, with sample spectra from the designated protein spot shown in FIG. 5C. The concentration of R6G in this protein spot was determined to be 3.1 nM, averaged over the gel volume with dimensions as drawn in FIG. 5B. The detection limit was defined as 3× noise and routinely set at 0.2 nM. The Raman intensity image for this gel region (FIG. 5D) accurately represented the fluorescence image (FIG. 5B), and the Raman spectrum shown in FIG. 5E was obtained from the selected protein spot containing 3.1 nM R6G.

GMP Synthetase Isoforms.

Recombinant hGMPS protein species were compared with endogenous proteins in unlabeled, SyproRuby stained 2-D gels. The recombinant protein was purified as multiple species termed here as "isoforms". By fluorescence densitometry quantification using SyproRuby staining, the hGMPS protein species identified as E1-E4 in FIG. 6B comprised 0.1-0.2% of the total 200 µg protein lysate, or 200-400 ng, in the gel. Four species were also identified in recombinant hGMPS purified from an $E.$ $coli$ expression system (labeled R1-R4 in FIG. 6C). The species of the recombinant protein resembled those found in endogenous HCT116 cell lysate as shown after 2-DGE separation. The mass distribution among endogenous isoforms of hGMPS, with the most abundant species E2 (FIG. 6B) was pI-shifted to a more acidic form relative to the major recombinant species (R1 in FIG. 6C). One interpretation would be that the most basic recombinant hGMPS species (R1) was an unmodified or native parent species, while the remaining putative hGMPS isoforms (2-4) were likely to be modified versions of this protein found in the endogenous sample.

Quantification of hGMPS Isoforms in Lysate.

To evaluate the ratiometric quantification strategy in typical proteomic samples, an imaging-based internally standardized analysis was designed to quantify small-fold changes in hGMPS isoform distribution with a constant protein background in a complex cell lysate. In this experiment, two pairwise ratiometric analyses were performed with recombinant hGMPS spiked lysates. The tasks were to determine both the accuracy in % d4-R6G composition for multiple hGMPS species and the composition of endogenous hGMPS in the lysate.

Figure 7:
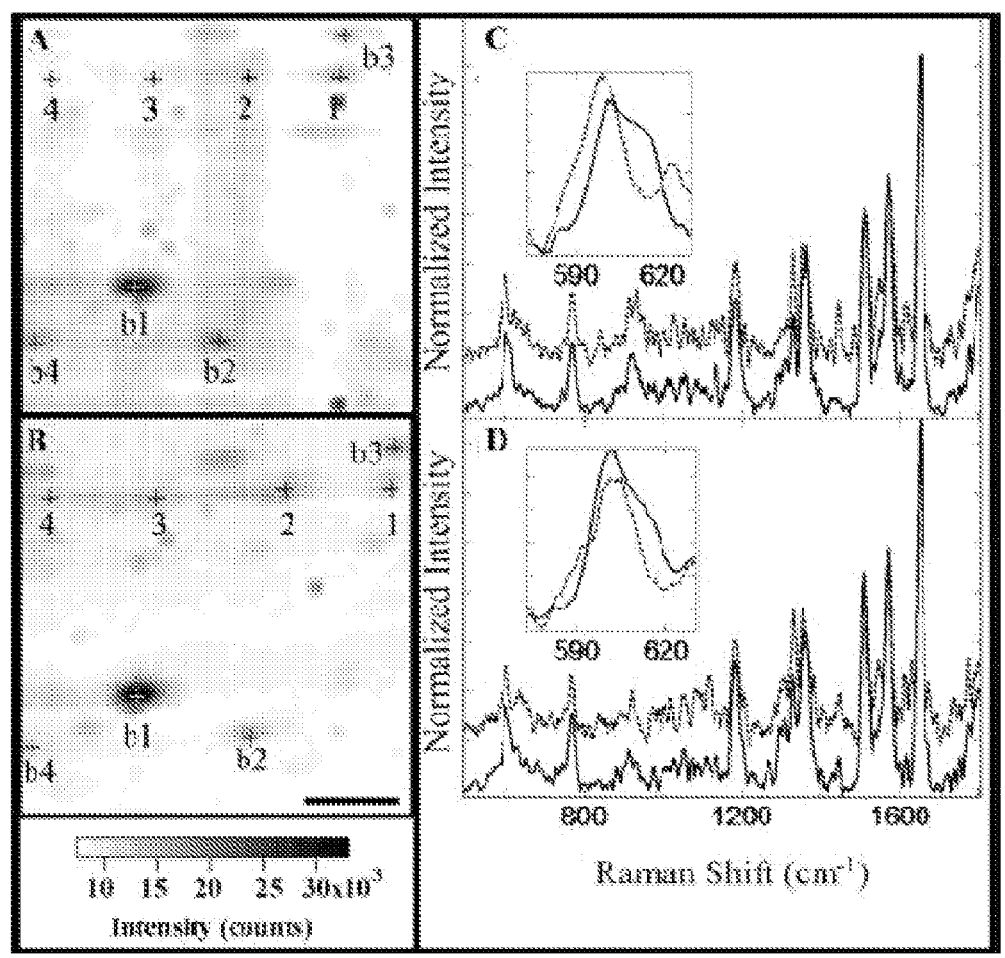
FIG. 7 illustrates Raman mapping images for samples A and B, in panels A and B respectively. Protein species labeled 1-4 in samples A and B were confirmed to be hGMPS by in gel trypsin digestion and MS/MS peptide sequencing. Also shown are the background lysate proteins, labeled b1-b4, selected for % d4-R6G composition calculations. Scale bar represents 2.5 mm. Representative baseline-corrected SERRS spectra from samples A and B are shown in panels C and D, respectively. Signal from the background protein species b1 (solid trace) is compared with signal from the hGMPS species 1 (dashed trace). The inset shows the signature d0-R6G (611 cm$^{-1}$) and d4-R6G (600 cm$^{-1}$) peaks, with d4-R6G signal enrichment in the dashed hGMPS species traces as expected in these spiked samples.
Figure 8:
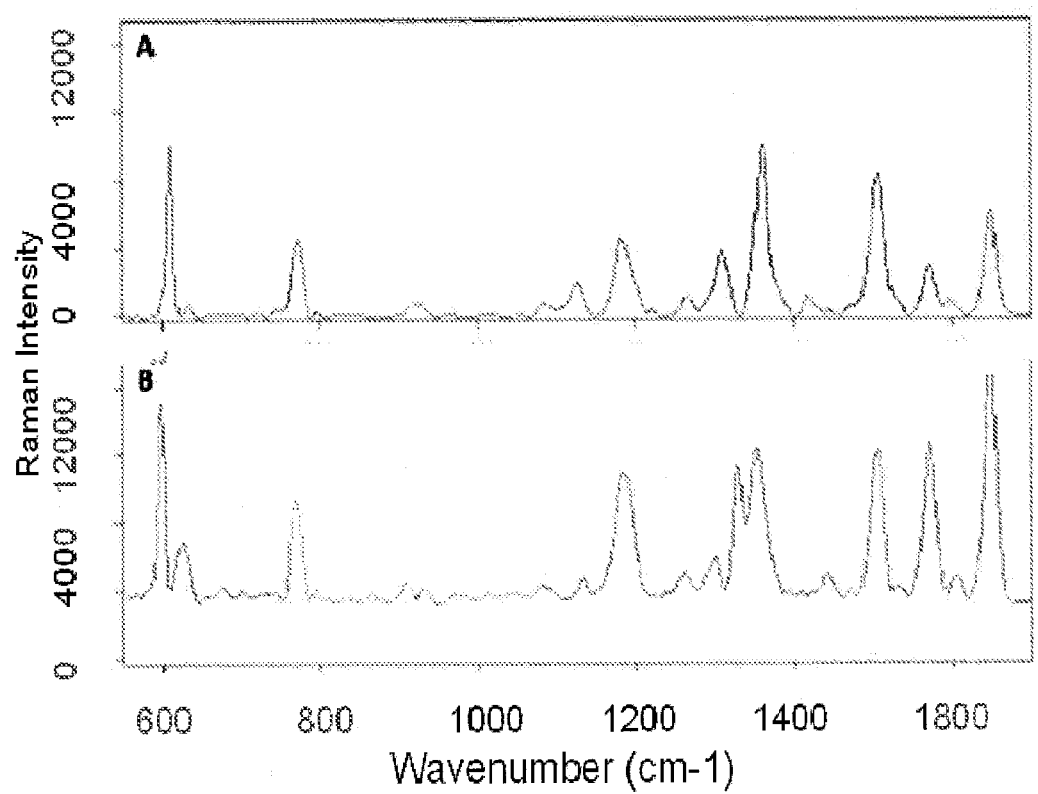
FIG. 8 is the baseline corrected SERRS spectra. (A) pure d0-R6G. (B) d4-R6G labeled proteins. The spectra were obtained on a Senterra Raman detection system (Bruker Optics) using a 532 nm laser (settings 5 mW power, 60 second integration time, 5 coadditions, and using spectral resolution of 3-5 cm$^{-1}$). The total amount of protein deposited onto the membrane was 400 ng.

SERRS imaging was used for direct quantification of d4-R6G composition in mixed lysate samples containing 0%, 0.2%, or 0.4% mass-spiked hGMPS, analyzed as samples A and B. The results reported in Table 1 were based upon single gel analyses for samples A and B (FIG. 7). Each pixel in FIG. 7 represents a full R6G Raman (SERRS) spectrum. Representative SERRS spectra that compose the image maps of samples A and B are shown in FIG. 7. These spectra (48× 48=2304 per image) were fitted using a partial least-squares analysis that had been modeled using a training set of 1000 spectra recorded at controlled % d4-R6G compositions. The % d4-R6G compositions in each of the hGMPS and background species (Table 1) were calculated by PLS analysis and averaged over three spectra per protein spot. As a measure of overall variance for this ratiometric quantification imaging method, the total RSD % were determined separately for samples A and B, using the average and standard deviations of replicate readings for the eight identified protein species reported in Table 1. For both samples A and B, the total RSD % are 16%.

TABLE 1

Percent d4-R6G Composition in hGMPS and Background Protein Species in Samples A and B, Determined by Full-Spectral Raman Analysis.

| protein species | % d4 (sample A) | % d4 (sample B) |
| --- | --- | --- |
| 1 | 86 ± 4 | 66 ± 5 |
| 2 | 76 ± 8 | 60 ± 5 |
| 3 | 70 ± 2 | 56 ± 9 |
| 4 | 50 ± 9 | 49 ± 9 |
| b1 | 46 ± 8 | 45 ± 3 |
| b2 | 43 ± 8 | 52 ± 8 |
| b3 | 40 ± 13 | 46 ± 15 |
| b4 | 46 ± 1 | 57 ± 5 |

Figure 6:
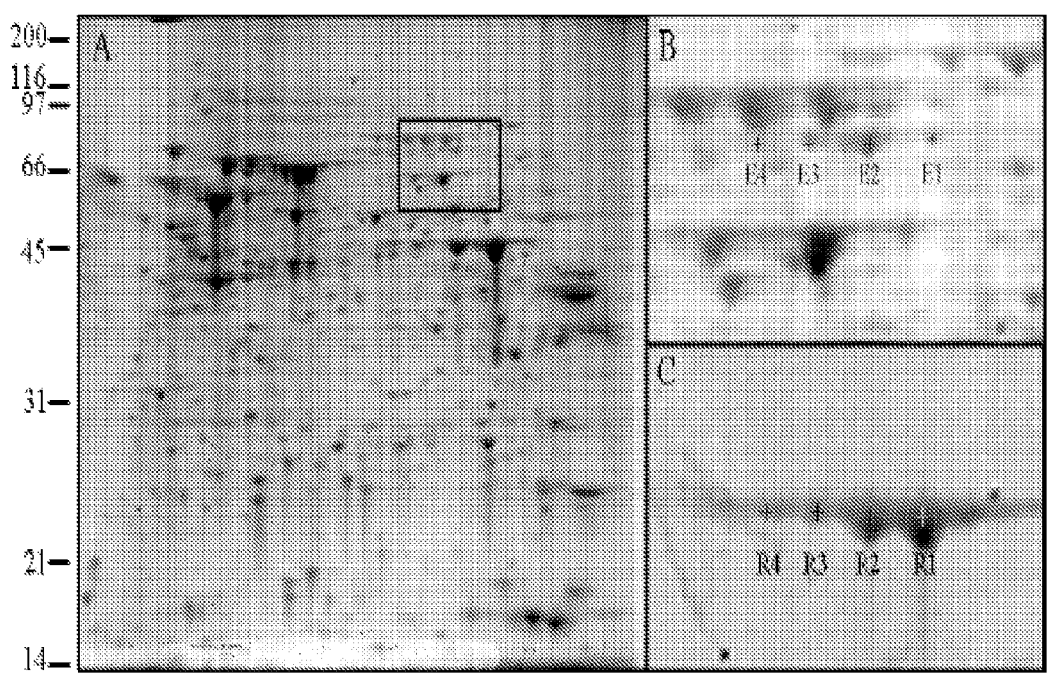
FIG. 6 illustrates a comparison between endogenous and recombinant hGMPS protein species in unlabeled, Sypro-Ruby stained 2-D gels. (A) The full-scale fluorescence image of 200 μg of HCT116 lysate was recorded using a Typhoon scanner. (B) The inset region of panel A was enlarged and contrasted to show putative endogenous species of hGMPS, labeled E1-E4. (C) The 2-DGE image of 1 μg of recombinant hGMPS is shown on the same scale as panel B and contained four distinct species of hGMPS(R1-R4).

Recombinant hGMPS (R) was quantified independently by fluorescence densitometry analysis of the 2-DGE analysis shown in FIG. 6C and with knowledge of the protein concentration. Given the Raman measured % d4-R6G compositions reported in Table 1, the endogenous hGMPS (E) values were calculated using equations (1) and (2), reported in Table 2. For the least abundant hGMPS species (species 4), the endogenous amount could not be determined due to the low abundance in the recombinant internal standard.

TABLE 2

Quantification of Endogenous Isoforms of hGMPS species (E) in Samples A and B, as Directly Determined from SERRS Spectra and Using Recombinant Protein (R) as an Internal Standard.

| hGMPS species | Recombinant[a] (R) (ng/100 ng) | Endogenous (E(Sample A)) (ng/100 µg lysate) | Endogenous (E(Sample B)) (ng/100 µg lysate) |
| --- | --- | --- | --- |
| 1 | 46.2 | 35.2 ± 2.5 | 34.6 ± 3.8 |
| 2 | 36.5 | 66.2 ± 9.6 | 65.5 ± 7.1 |
| 3 | 12.6 | 38.1 ± 1.5 | 37.2 ± 8.1 |
| 4 | 0.6 | nc[b] | nc[b] |

[a] Recombinant protein distribution was normalized to 100 ng, equivalent to 0.1% w/w in 100 µg lysate.
[b] The value of endogenous protein species 4 could not be calculated (nc).

Example 4

Protein Labeling and SERRS Spectrum of Isotopic Variants of R6G-transferrin in PVDF Preparation of R6G Labeled-Proteins. Protein labeling experiments with the R6G-NHS ester labeling reagents were performed using human transferrin as an example protocol. To ~1.5 mg protein (T3309 human transferrin, apo form, Sigma, St. Louis, Mo.) in 1 mL of 50 mM borate buffer (pH 8.5) was added the various isotopic versions of R6G-NHS ester labeling reagent in dimethylsulfoxide (DMSO). The reaction was protected from light and incubated at room temp for 1 h. The sample was then desalted on PD10 (Amersham, G-25 resin, GE Healthcare, Piscataway, N.J.) columns into 50 mM Tris, 100 mM NaCl, 1 mM EDTA pH 7.5. The protein fraction was collected and concentrated on a 5 k MWCO ultrafree spin filter (Millipore), and buffer exchange was repeated 3 times to remove excess dye. The conditions provided labeling efficiency of 1-2%. Other example proteins used for these studies include RNAse A and anti-transferrin antibody. Labeling efficiencies were adjusted from 0.1% to 100% by altering the relative amounts of labeling reagent in the reactions.

Staining of d0-, d4-, d6-R6G-transferrin on PVDF Membrane Thin strips of PVDF membranes were cut and labeled in pencil for registration of sample spots. The membrane was soaked in 100% methanol for 1 min until transparent, then placed in water for at least 10 min, until hydrated. The R6G-labeled transferrin was diluted in a 5 times dilution series, and 1 µl of the protein was analyzed in a dot blot format. After protein deposition, the membranes were dried, and blocked in a 0.3% solution of Tween 20. Staining was performed using gold and silver staining. Several methods for the deposition of silver particles can be used. An example method uses is the silver enhanced protogold stain (Sorensen, B. K. et al. (2002) "Silver Staining of Proteins on Electroblotting Membranes and Intensification of Silver Staining of Proteins Separated by Polyacrylamide Gel Electrophoresis" Anal. Chem. 304, 33-41.) Briefly aural chloride solution is incubated with the membranes for 2 to 4 h until the visible appearance of gold stain on the protein spots. Gold particles are localized by their affinity for protein; addition of silver enhancing reagent that coats the gold surfaces further increases the nanoparticle affinity for the R6G and supports SERRS.

Figure 9:
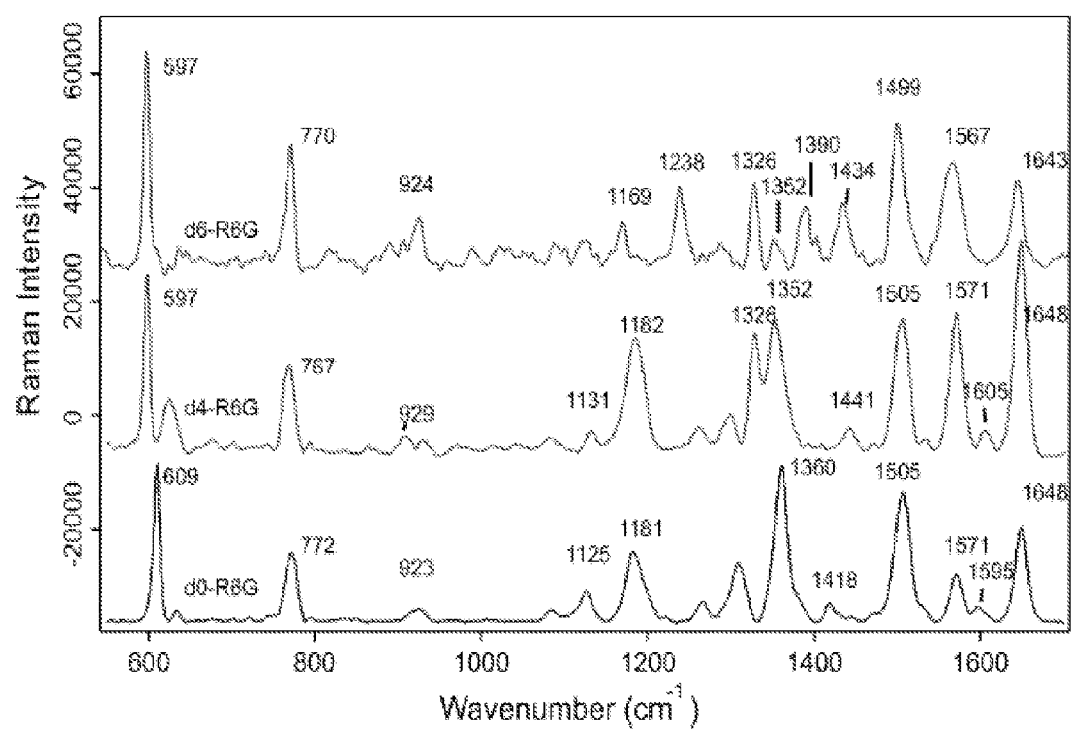
FIG. 9 illustrates the comparison of d6-R6G spectrum from labeled transferrin in PVDF membrane with d0- and d4-R6G spectra from labeled RNaseA in PVDF. The peak of ring in plane bending in d0-R6G labeled transferring (615 cm$^{-1}$) was shifted to 597 (cm$^{-1}$) in d4 and d6-R6G labeled transferrin. The C—H bending peak (772 cm$^{-1}$) in d0-R6G labeling were shifted to 767 and 770 cm$^{-1}$ in d4-R6G and d6-R6G labeling. There are also a number of peak shifts in the aromatic C—C stretch of Raman signals.

Raman Spectra Acquisition and Analysis. The SERRS spectra were obtained using Bruker Senterra Raman (with 0.2 mW at the sample). The integration time for R6G is 20 s with a co-addition factor of 5. As shown in FIG. 9, the Raman spectrum of d6-R6G labeled transferrin is distinguished from those of d0-R6G and d4-R6G labeled protein. Several Raman bands are shifted in the d6-R6G spectrum compared to d0-R6G and d4-R6G. A full description of the chemical bond structure origin of the observed Raman bands is provided in Jensen L., and Schatz, G. C. (2006) J. Phys. Chem. Lett. A 110, 5973-7.

Figure 10:
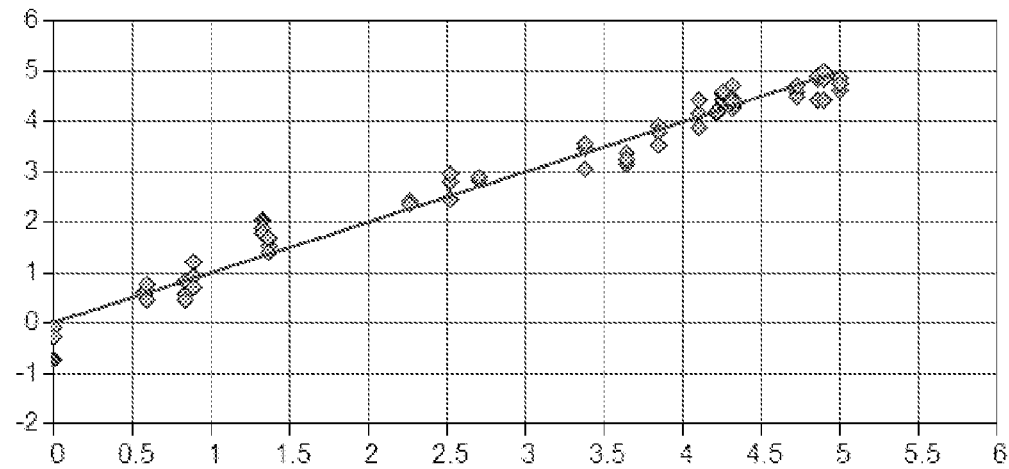
FIG. 10 are plots of predicted versus true dye concentration from d0 and d4 labeled protein spotted onto PVDF membranes and stained. Units are given in picomoles (samples derived from protein samples at micromolar concentrations).
Figure 10:
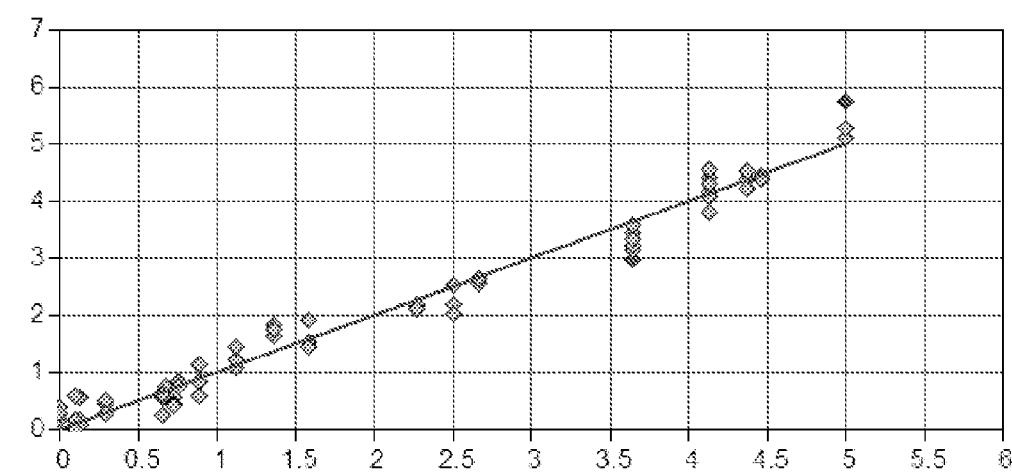

D0/D4 ratio quantification. To demonstrate labeled protein quantification in PVDF, a set of twenty samples were prepared at a total concentration of 5 µM dye containing varied amounts of d0 and d4-R6G-labeled protein (in this case RNaseA). Again 1 µl aliquots were spotted onto an Immobilon FL membrane, and stained according to the gold/silver protocol used previously. The spectra were collected using the same settings reported above (0.2 mW, 10 second integration time, 1 scan), then used to model using full spectral partial least squares calibration (PLS). Shown in FIG. 10 are two plots demonstrating the predicted versus true concentrations of either d0 or d4-R6G in the twenty training samples. This model can be improved by training with additional spectra recorded at lower concentrations; however these results are acceptable to analyze R6G-labeled protein mixtures in Table 3.

The model was applied to a series of spectra from mixed samples containing 0, 25, 33, 50, 66, 75, or 100% d0 and d4-R6G labeled transferrin. Shown in Table 3 are the expected and calculated values for the d0 and d4 components. This model is refined by using larger training sets to include the lower concentration ranges (below 0.2 µM).

TABLE 3

Composition of d0- and d4-R6G-labeled transferrin and the estimated composition using the first version of our PLS model trained as described above, reported for three readings as average and standard deviation.

| Expected | | Observed | | | |
| --- | --- | --- | --- | --- | --- |
| D0 | D4 | D0 | stdev | D4 | stdev |
| 4.7 | 0 | 4.57 | .36 | −.52 | 0.48 |
| 3.5 | 1.3 | 4.10 | .23 | 1.44 | 0.26 |
| 3.1 | 1.7 | 3.94 | .19 | 1.80 | 0.41 |
| 2.3 | 2.6 | 2.86 | .40 | 2.98 | 0.59 |
| 1.5 | 3.4 | .99 | .63 | 1.71 | 1.32 |
| 1.2 | 3.9 | 1.29 | .46 | 3.51 | 0.59 |
| 0 | 5.1 | .00 | .12 | 4.38 | 0.40 |

Figure 11A:
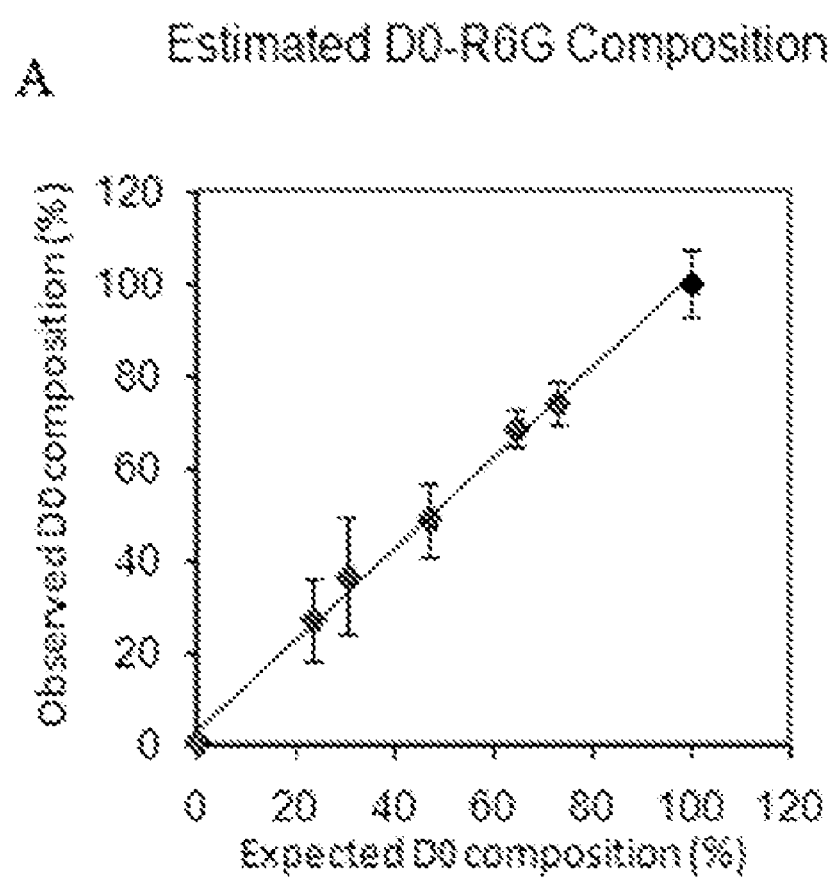
FIG. 11 shows the calculation of % d0-R6G composition in d0 and d4-R6G labeled transferrin samples at 5 µM dye composition (or 5 pmol deposited per PVDF membrane spot). The percent composition of d0- and d4-R6G-labeled transferrin was calculated and shown in FIG. 3A.
Figure 11B:
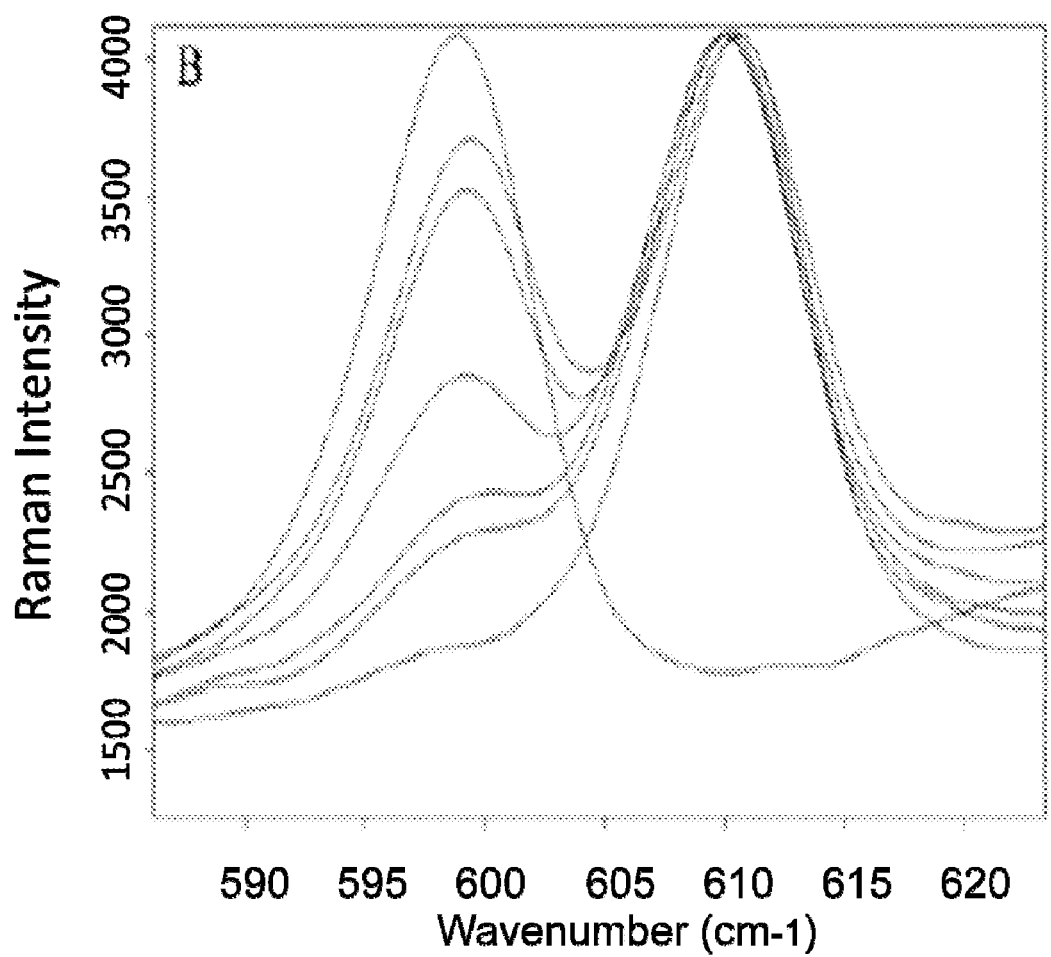
Figure 12:
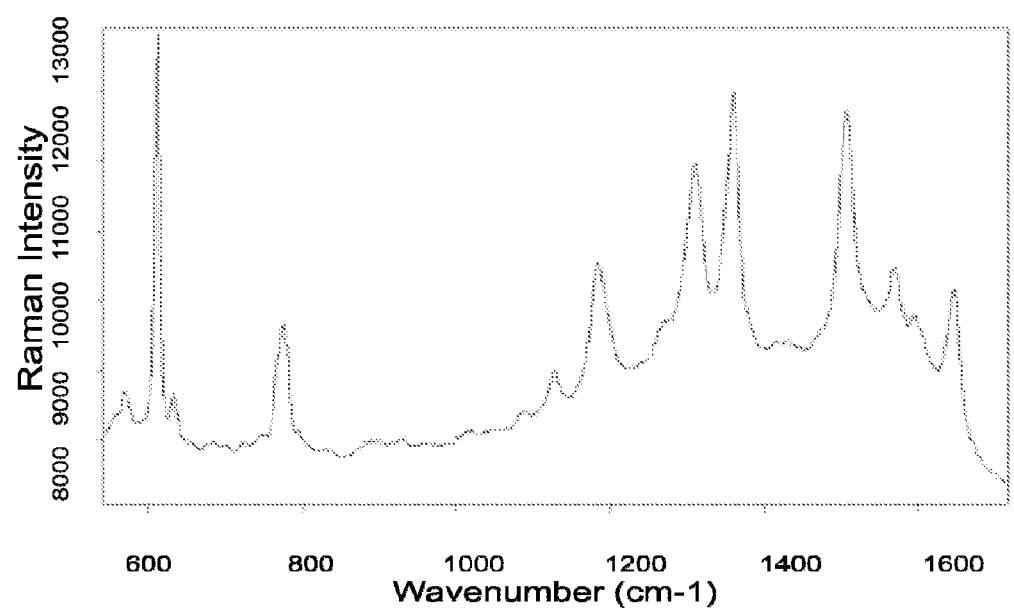
FIG. 12 is the SERRS spectra of d0-R6G labeled protein on a PVDF membrane. A 633 nm laser was used.

In a different representation of the data in Table 3, an alternate method for quantification involving peak integration has been demonstrated for a two component mixture. Note that the full spectral PLS model approach is expected to be more useful for multiplexed analyses because it uses all spectral information from the data to estimate percent composition. As demonstrated for previous experiments, pure d0- or d4-R6G labeled proteins were combined in controlled mixtures, and subjected to a quantification analysis. Spectral acquisition times were significantly shortened on PVDF membrane, using the following settings: 0.2 mW power, 10 second integration time, and a single co-addition, and spectral resolution of 3-5 cm$^{-1}$. Spectra obtained for samples combined at 0, 25, 33, 50, 66, 75, and 100% d0-R6G composition could then be modeled using a principal least squares analysis. Error bars show standard deviation for estimated values. Shown in FIG. 11A is a plot of observed versus expected % d0-R6G composition. In FIG. 11B is enlarged region of the Raman spectra focused on the 580-630 cm$^{-1}$ frequency window which includes signature d0- and d4-R6G peaks.

R6G Labeled Oligonucleotide. Oliogonucleotides (example sequence 5'-AGAGTTTGATCCTGGCTCAG-3') were synthesized with 5'-6-aminohexanyl function group attached. (Rhodamine 6G-6-[carboxy-(N-hydroxysuccinimidyl)]-N-(methyl)-hexyl amide) was reacted with the 5'-modified oligonucleotide in sodium carbonate and sodium bicarbonate buffer (pH 8.5). The mixture of modified oligo and R6G dye (1:1.5 molar ratio) was seated at room temperature for one hour. After reaction, the mixture was purified on PD-10 column (GE healthcare). The collected dye labeled oligonucleotide was concentrated on a micron filter (Millipore), washed with Millipore pure water, and resuspended in PBS buffer (pH 7.4).

Figure 13:
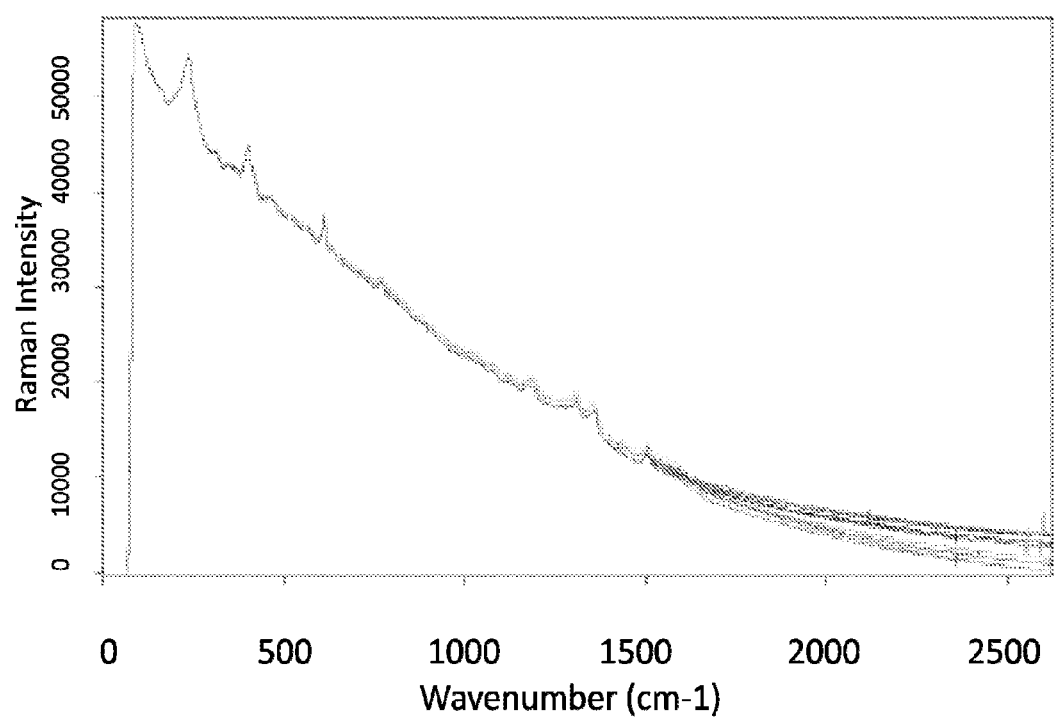
FIG. 13 illustrates the uncorrected (raw) SERS spectra of hybridized R6G labeled oligo with target DNA on a PVDF membrane. The data were collected using the SENTERRA confocal Raman system (Bruker Optics Inc, Billerica Mass.) with a 50× air objective and a 785 nm laser operated at 50 mW power, integration time of 30 s and spectral resolution is 3 to ~5 cm$^{-1}$.

Raman spectrum of R6G labeled DNA on PVDF membrane. DNA-Gold-R6G probes were synthesized using the following procedure. R6G labeled DNA oligonucleotides were added to the red oily precipitate obtained from 10 mL of gold colloid and 1 mL of 6-mercaphexanol (1 µM) to result in a 1 mL solution with a final oligonucleotide concentration of 1 µM. After 24 h, the solution was buffered at pH 7.5 (10 mM phosphate buffer with 0.01% Tween 20). After 30 min, 3 M NaCl was slowly added over 30 min until the desired salt concentration (0.3 M) was obtained. The solution was further seated under these conditions for an additional 24 h, and the excess reagents were removed by centrifugation. Following the removal of the supernatant, the red oily precipitate was washed twice with 0.3 M NaCl, 0.01% Tween 20, 10 mM phosphate buffer (pH 7.5) (0.3 M PBS) by successive centrifugation and redispersion. The noncovalent addition (absorption) of the oligonucleotide to the gold was confirmed by measuring the difference in absorbance at 260 nm between the original DNA solution and the supernatant collected after centrifugation. The mixture was gently stirred for 24 h and then centrifuged for 20 min at 8000 rpm to remove the supernatant. After washing three times with 0.3 M PBS (pH 7.5), the final red oily precipitate of DNA-Gold-R6G was redispersed in the same buffer. A PCR product from amplification of bacterial 16 S RNA was denatured for 10 min in boiling water and chilled on ice. The sample (1 µL) was dot-blotted onto a Millipore PVDF membrane at concentrations of 1×10$^{-6}$ M. For ensemble measurements, 1 µL of the synthetic R6G-labeled DNA-Gold probes in PBS (pH 7.0) containing 140 mM NaCl in a final concentration of 1×10$^{-8}$ M. The mixed solutions on membrane were heated to 65° C. and slowly cooled down to 25° C. with a gradient of 0.4° C. per minute. After hybridization, the membrane was washed with Millipore water to remove the gold nanoparticles, which then subjected to silver coating and SERRS measurements. FIG. 13 shows the uncorrected spectra and the acquisition parameters are in the Figure legend.

Figure 14:
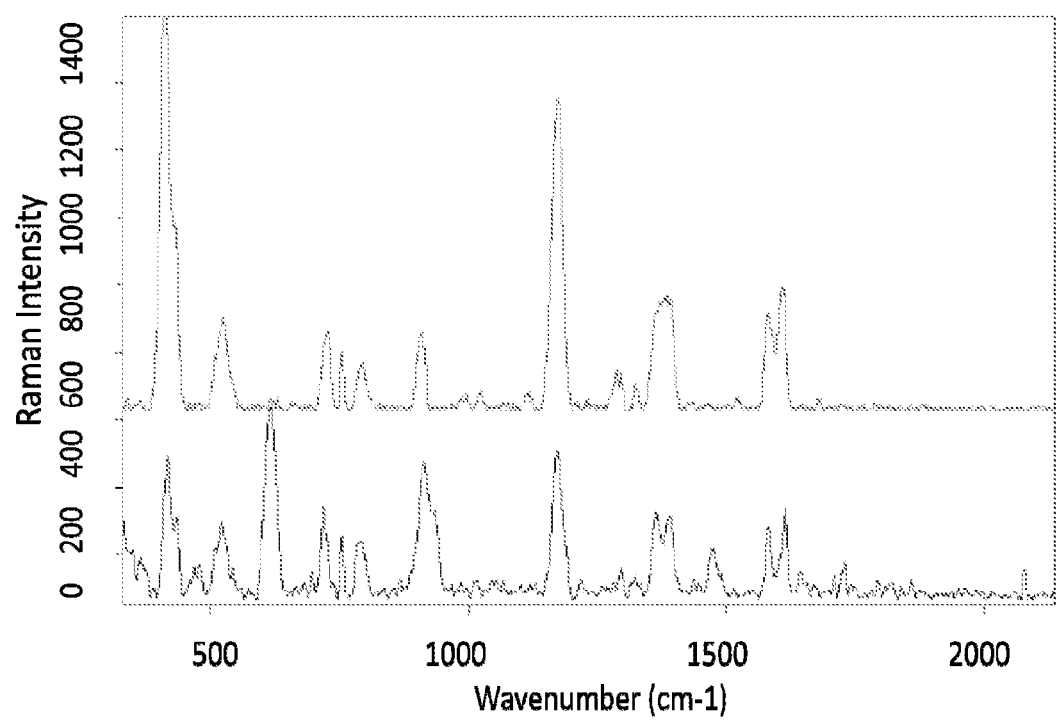
FIG. 14 illustrates the Raman (SERS) spectrum of Crystal Violet (CV) labeled transferrin on PVDF. The Raman spectra of Crystal Violet labeled transferring were recorded on a Bruker Senterra at 785 nm with 1 mw of power and 30 s integration time. Top is CV-labeled transferrin and bottom is CV free acid precursor to the NHS ester labeling reagent.

Preparation, Staining of Crysal Violet labeled transferrin on PVDF. The Crystal Violet labeling reactions for transferrin contained 1 mg protein in 1 mL of 50 mM borate buffer, pH 8.5, to which was added 100 nmole of d0-Cystal violet-NHS ester labeling reagent in dimethyl formamide (DMF). The reaction was protected from light and incubated at room temp for 1 h. Then the samples were desalted on PD10 (Amersham, G-25 resin) columns into 50 mM Tris, 100 mM NaCl, 1 mM EDTA pH 7.5. The protein fraction was collected and concentrated on a 5 k Mwco ultrafree spin filter, and buffer was exchanged at least 3× to assure that most of the excess dye was removed from the reactions. No denaturation (such as with 8M urea washes) were used because these proteins are meant to be applied in a native detection method. The labeled protein was then put onto a thin strip of membrane presoaked in methanol (100%) by pipetting 1 µL volume of sample onto the blot while the membrane is still damp. After allowing to air dry, membranes were rehydrated using water containing 0.3% Tween 20 and soaking 15 min for the Immobilon P and FL membranes, or more than 1 h for the PSQ membrane. After rinsing 3× in PBS (5 min each rinse), the membranes were placed as individual strips into 15 ml falcon tubes, and 2 mL of Quantigold solution was added to each tube. The tubes were agitated on a rotating mixer at room temp for 2-4 h, until the dark red staining of the protein spots were apparent before rinsing in water. A 1:1 solution of the silver stain enhancement reagents were, then transferred in 2 mL to each tube and kept on a rotating mixer for 3-5 min until silver stain is apparent. There membranes were then rinsed in water, allowed to air dry, and stored in the dark overnight before being analyzed by Raman. An example of SERS spectra are shown in FIG. 14.

It is intended that the foregoing detailed description be regarded as illustrative rather than limiting, and that it be understood that it is the following claims, including all equivalents, that are intended to define the spirit and scope of this invention.

The invention claimed is:

1. A compound of formula (II):

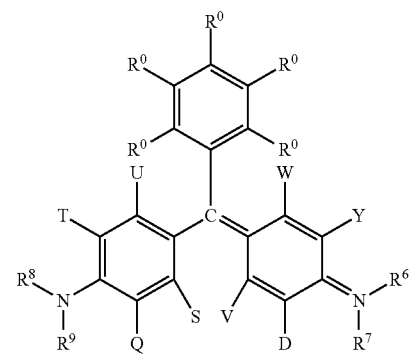

(II)

where $R^0$ is either X or of the formula (IIa):

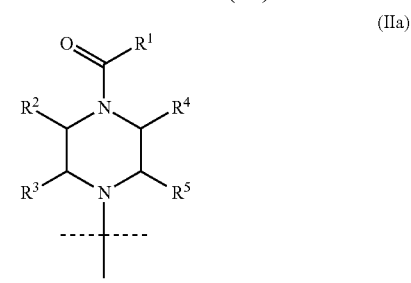

(IIa)

where Q, S, T, U, V, W, X, Y, and Z are each independently hydrogen, deuterium, halogen, substituted or unsubstituted $C_{1-20}$ alkyl, substituted or unsubstituted $C_{2-8}$ alkenyl, substituted or unsubstituted $C_{2-8}$ alkynyl, where at least one of Q, S, T, U, V, W, X, Y, and Z is deuterium, where $R^1$ is substituted or unsubstituted $C_{2-8}$ alkynyl, —R'N$_3$, —R'COOH, —R'C(O)OR'', —R'C(O)NH$_2$, —R'NCS, —R'NCO, —R'NH$_2$, —R'SH, —R'NC(O)CH$_2$I, or —R'C(O)O-succinimide, where $R^2$, $R^3$, $R^4$, $R^5$, $R^6$, $R^7$, $R^8$, and $R^9$ are each independently hydrogen, halogen, substituted or unsubstituted $C_{1-20}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, or substituted or unsubstituted 3- to 10-membered heterocyclyl, where $R^2$ and $R^3$, $R^4$ and $R^5$, $R^6$ and $R^7$, or $R^8$ and $R^9$ may, together with the atoms to which they are attached, form a substituted or unsubstituted 3- to 10- membered ring, and where R' and R" are each independently selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl.

2. The compound of claim 1, where one $R^0$ is of formula (IIa), and $R^1$ is —$(CH_2)_nN_3$, —$(CH_2)_nNH_2$, —$(CH_2)_n$COOH, —$(CH_2)_nC(O)OR''$, —$(CH_2)_nC(O)NH_2$, —$(CH_2)_n$NCS, —$(CH_2)_nNCO$, —$(CH_2)_nNH_2$, —$(CH_2)_nSH$, —$(CH_2)_n$ $NC(O)CH_2I$, —$(CH_2)_nC(O)O$-succinimide, —$(CH_2)_n$ C≡CH, —$(CH_2)_nAr^1$ NCS, —$(CH_2)_n$ $Ar^1$ $NH_2$, —$(CH_2)_n$ $NC(O)CH_2C$≡CH, or —$(CH_2)_nC(O)$$NCH_2CH_2SH$, and where n is 1-10, and $Ar^1$ is substituted or unsubstituted $C_{6-10}$ aryl, substituted or unsubstituted 5- to 10-membered heteroaryl, or substituted or unsubstituted 3- to 10-membered heterocyclyl.

3. The compound of claim 1, where the at least one of $R^0$ is of the formula (IIb):

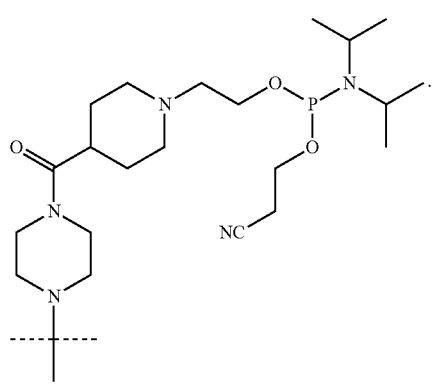

(IIb)

4. The compound of claim 1, where the at least one of $R^0$ is of the formula (IIc):

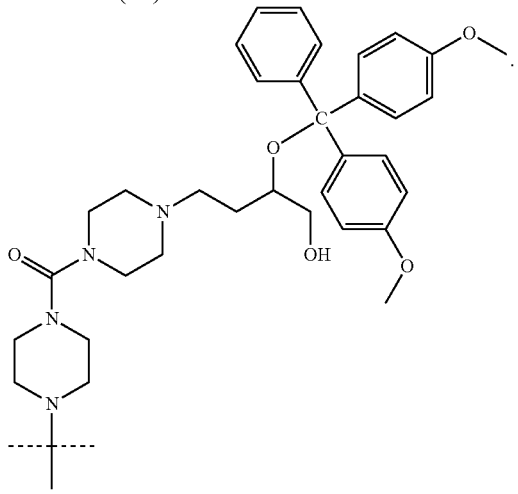

(IIc)

5. A compound of the formula (IId):

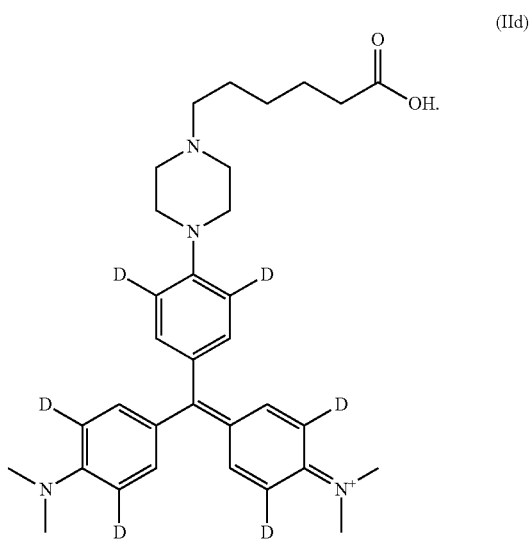 [SMILES: [2H]C1=CC(=C(c2cc([2H])c(N(C)C)c([2H])c2)c2cc([2H])c(N3CCN(CCCCCC(=O)O)CC3)c([2H])c2)C=C([2H])C1=[N+](C)C]

(IId)

6. The compound of claim 1, wherein the deuterated compound is obtained from a deuterated precursor.

7. The compound of claim 1, wherein the deuterated compound is obtained by isotopic exchange of aromatic protons between an organic dye and a deuterated acidic media.

8. A method for evaluating a sample comprising the steps of: labeling at least a portion of an analyte with the compound of claim 1, and detecting the labeled portion, wherein the analyte is selected from the group consisting of proteins, nucleic acids, lipids, and structural mimetic thereof, fragments thereof, or metabolites thereof.

9. The method of claim 8, further comprising a step of:
labeling at least a portion of the analyte with a non-isotopic compound,
where the non-isotopic compound has the same chemical structure as the compound in claim 8, and only differs in non-isotopic substitution.

10. The method of claim 8, further comprising a step of: separating the analyte from the sample.

11. The method of claim 8, further comprising a step of: applying particles onto the analyte.

12. The method of claim 8, further comprising a step of: applying the analyte onto a substrate.

13. The method of claim 10, wherein the separating is selected from the group consisting of sodium dodecyl sulfate-polyacrylamide gel electrophoresis (SDS-PAGE), two-demensional SDS-PAGE (2DGE), and western blot.

14. The method of claim 11, wherein the particles comprise a metallic material.

15. The method of claim 14, wherein the metal material is copper, silver, or gold.

16. The method of claim 12, wherein the substrate comprises a semi-permeable or a permeable surface.

17. The method of claim 16, wherein the substrate is selected from the group consisting of polymeric membranes, polymeric gels, and polymeric beads.

18. The method of claim 17, wherein the substrate is nitrocellulose, polyvinylidene fluoride (PVDF), or polysulfone.

19. The method of claim 18, wherein the analyte is specific xenobiotic chemicals derived from cells, bodily fluids, or tissues.

20. The method of claim 8, wherein the analyte is pharmaceuticals, or environmental samples.

21. A method of multiplex analysis, comprising:
    labeling a plurality of analytes with at least two compounds of claim 1, and
    detecting the labeled analytes.

\* \* \* \* \*